US009766217B2

(12) United States Patent
Kidal et al.

(10) Patent No.: US 9,766,217 B2
(45) Date of Patent: Sep. 19, 2017

(54) METHODS OF OPTIMIZING CHROMATOGRAPHIC SEPARATION OF POLYPEPTIDES

(75) Inventors: Steffen Kidal, Copenhagen F. (DK); Thomas Budde Hansen, Copenhagen N. (DK); Arne Staby, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 897 days.

(21) Appl. No.: 12/440,242

(22) PCT Filed: Sep. 8, 2007

(86) PCT No.: PCT/EP2007/059432
§ 371 (c)(1),
(2), (4) Date: May 1, 2009

(87) PCT Pub. No.: WO2008/028974
PCT Pub. Date: Mar. 13, 2008

(65) Prior Publication Data
US 2010/0004907 A1    Jan. 7, 2010

Related U.S. Application Data

(60) Provisional application No. 60/844,012, filed on Sep. 12, 2006, provisional application No. 60/918,804, filed on Mar. 19, 2007.

(30) Foreign Application Priority Data

Sep. 8, 2006 (EP) .................................... 06120379
Mar. 16, 2007 (EP) .................................... 07104316

(51) Int. Cl.
*G06F 17/10* (2006.01)
*G01N 30/86* (2006.01)
*C07K 1/16* (2006.01)
*G06K 9/00* (2006.01)

(52) U.S. Cl.
CPC .......... *G01N 30/8693* (2013.01); *C07K 1/16* (2013.01); *G06K 9/00536* (2013.01)

(58) Field of Classification Search
None
See application file for complete search history.

(56) References Cited

U.S. PATENT DOCUMENTS 5,666,297 A    9/1997 Britt et al.

OTHER PUBLICATIONS

Iyer et al. Journal of Chromatography A, 832, 1-9, 1999.*
Brooks, C.A. et al., "Steric Mass-Action Ion Exchange: Displacement Profiles and Induced Salt Gradients", AIChE Journal, 1992, vol. 38, No. 12, pp. 1969-1978.
Ciien, W.D. et al., "Modeling of the Whole Expanded-Bed Protein Adsorption Process with Yeast Cell Suspensions as Feedstock", Journal of Chromatography, 2003, vol. 1012, pp. 1-10.
Gadam, S.D. et al., "Characterization of Non-Linear Adsorption Properties of Dextran-Based Polyelectrolyte Displacers in Ion-Exchange Systems", Journal of Chromatography, 1993, vol. 630, pp. 37-52.
Gallant, S.R. et al., "Optimization of Preparative Ion-Exchange Chromatography of Proteins: Linear Gradient Separations", Journal of Chromatography, 1996, vol. 725, pp. 295-314.
Hodges, R.S. et al., "Computer Simulation of High-Performance Liquid Chromatographic Separations of Peptide and Protein Digests for Development of Size-Exclusion, Ion-Exchange and Reversed-Phase Chromatographic Methods", Journal of Chromatography, 1988, vol. 458, pp. 147-167.
Jakobsson, N. et al., "Using Computer Simulation to Assist in the Robustness Analysis of an Ion-Exchange Chromatography Step", Journal of Chromatography, 2005, vol. 1063, pp. 99-109.
Jakobsson, N. et al., "Optimisation and Robustness Analysis of a Hydrophobic Interaction Chromatography Step", Journal of Chromatography, 2005, vol. 1099, pp. 157-166.
Karlsson, D. et al., "Methodologies for Model Calibration to Assist the Design of a Preparative Ion-Exchange Step for Antibody Purification", Journal of Chromatography, 2004, vol. 1033, pp. 71-82.
Karlsson, D. et al., "Model-Based Optimization of a Preparative Ion-Exchange Step for Antibody Purification", Journal of Chromatography, 2004, vol. 1055, pp. 29-39.
Kempe, H. et al., "Simulation of Chromatographic Processes Applied to Separation of Proteins", Journal of Chromatography, 1999, vol. 846, pp. 1-12.
Langmuir, I., "The Adsorption of Gases on Plane Surfaces of Glass, Mica and Platinum", Journal of the American Chemical Society, 1918, vol. 40, No. 9, pp. 1361-1402.
Lim, Y.I. et al, "Computer-aided Model Analysis for Ionic Strength-Dependent Effective Charge of Protein in Ion-Exchange Chromatography", Biochemical Engineering Journal, 2005, vol. 25, pp. 125-140.
Liu, X. et al., "Modeling of Preparative Reversed-Phase HPLC of Insulin", Biotechnology Progress, 2002, vol. 18, pp. 796-806.
Quinones-Garcia, I. et al., "Performance Comparison of Suspended Bed and Batch Contactor Chromatography", Journal of Chromatography, 2001, vol. 908, pp. 169-178.
Perry and Green, Chemical Engineer's Handbook, 7$^{th}$ Edition, Chapter 16, Mc-Graw-Hill, New York.
Rege, K. et. al., "Predicting Column Performance in Displacement Chromatography from High Throughput Screening Batch Experiments", Separation Science and Technology, 2003, vol. 38, No. 7, pp. 1499-1517.
Wiesel, A. et al., "Modelling Gradient Elution of Bioactive Multicomponent Systems in Non-Linear Ion-Exchange Chromatography", Journal of Chromatography, 2003, vol. 1006, pp. 101-120.
Zhang, S. et al., "Steric Mass-Action Model for Dye-Ligand Affinity Adsorption of Protein", Journal of Chromatography, 2002, vol. 957, pp. 89-97.

(Continued)

*Primary Examiner* — Michael Borin
(74) *Attorney, Agent, or Firm* — Leon Y. Lum

(57) ABSTRACT

Described are methods for determination of peptide specific parameter(s) of a mixture comprising a target peptide and a related impurity (or impurities) to be used in a simulation model of chromatographic separation using mathematical model(s). Also described are chromatographic simulation methods using above determined parameters, as well as computer systems and computer programs for performing one or more of the above method(s).

9 Claims, 20 Drawing Sheets

(56) References Cited

OTHER PUBLICATIONS

S. Kidal et al., Poster presented at PREP 2006 in Baltimore MA, May 2006, "Simulation of an Industrial Ion Exchange Step (Part 2): The Use of Simulation for Scale-Up and Troubleshooting.", 2006.
T.B. Hansen et al., Poster presented at ACS 232nd ACS National Meeting & Exposition, "Simulation of an Industrial Ion Exchange Step: The Use of Simulation for Optimization.", 2006.
T.B. Hansen et al., Poster presented at PREP 2006 in Baltimore MA, May 2006, "Simulation of an Industrial Ion Exchange Step (Part 1): Determination of the Most Relevant Parameters.", 2006.
Staby et al. Comparison of weak Anion-Exchange Resins for Protein Purification. Oral presentation to be presented at ACS 232nd ACS National meeting & Exposition in San Francisco CA. Sep. 2006. In Preparation.

* cited by examiner

METHODS OF OPTIMIZING CHROMATOGRAPHIC SEPARATION OF POLYPEPTIDES

CROSS-REFERENCE TO RELATED APPLICATIONS

This application is a 35 U.S.C. §371 national stage application of International Patent Application PCT/EP2007/059432 (published as WO 2008/028974 A1), filed Sep. 8, 2007, which claimed priority of European Patent Application No. 06120379.0, filed Sep. 8, 2006 and European Patent Application No. 07104316.0, filed Mar. 16, 2007; this application further claims priority under 35 U.S.C. §119 of U.S. Provisional Application No. 60/844,012, filed Sep. 12, 2006 and U.S. Provisional Application No. 60/918,804, filed Mar. 19, 2007.

FIELD OF THE INVENTION

The present invention relates to simulation of chromatographic separation using mathematical models.

BACKGROUND OF THE INVENTION

Chromatography is a dynamic technique for separation of molecules, both analytically and in preparative scale, using gas or liquid as the mobile phase. For separation of proteins and polypeptides, liquid chromatography (LC) can be used in various modes such as, e.g., ion-exchange, reversed phase, hydrophobic interaction, affinity, and metal chelate chromatography, depending on the nature and ligands of the stationary phase. Ion-exchange chromatography primarily separates proteins based on their overall and/or local difference in charge, reversed phase and hydrophobic interaction chromatography separate proteins based on hydrophobicity of the proteins and polypeptides, while affinity chromatography (and many other modes of chromatography) separate proteins and polypeptides based on various attracting and repelling forces, including hydrogen binding, van der Waals, ionic and hydrophobic forces.

In analytical LC, loading of the chromatographic column is usually low to obtain the best possible separation of the distinct molecules present in the sample, and various elution gradients and modifiers are applied to achieve maximum resolution. In preparative LC, column loading is usually high to optimize productivity and process economy, and the separation procedure is designed to obtain optimal purity and yield of the target protein or polypeptide. Gradients and modifiers are usually applied in the most simplistic way possible to obtain the purity and yield desired. The nature of gradients in LC is linked to the mode of operation, e.g. salt and/or pH in ion-exchange chromatography, organic solvent in reversed phase chromatography, etc.

For many years, there has been a desire to adequately describe the very complex LC separation process using mathematical models for simulation of chromatographic separation. Key elements in such mathematical models include the adsorption isotherm describing solute equilibrium between the stationary and mobile phase, the overall mass balance of the chromatographic system, and an expression describing mass transfer from the mobile to the stationary phase (Perry and Green, Perry's Chemical Engineers' Handbook, Chap. 16, 7th Ed., McGraw-Hill, New York, 1997). The most recognized and applied adsorption isotherms today are those developed by Langmuir, J. Am. Chem. Soc. 40 (1918) 1361 (Langmuir isotherms) and Brooks and Cramer, AIChE J. 38 (1992) 1969-1978 (steric mass action (SMA) isotherms), and various derived expressions hereof for reversed phase and hydrophobic interaction chromatography and for ion-exchange chromatography, respectively.

Modelling has been applied to ion-exchange chromatography model systems (Karlsson et al., J. Chromatogr. A 1055 (2004) 29-39), hydrophobic interaction chromatography model systems (Jakobsson et al., J. Chromatogr. A 1099 (2005) 157-166), pseudo-affinity chromatography model system (Zhang and Sun, J. Chromatogr. A 957 (2002) 89-97, and reversed phase chromatography model system (Liu et al., Biotechnol. Prog. 18 (2002) 796-806). The latter publication described modelling of an artificial mixture of recombinant human, porcine, and human analogue insulin, and Wiesel et al. (J. Chromatogr. A 1006 (2003) 101-120) have published a modelling work with ion-exchange chromatography using an unspecified bioactive substance. Usually, however, research and verification of mathematical models are typically performed on model and non-biopharmaceutical protein mixtures, e.g. chymotrypsinogen and cytochrome c (Brooks and Cramer, AIChE J. 38 (1992) 1969-1978) and BSA (Chen et al., J. Chromatogr. A 1012 (2003) 1-10 and Lim et al., Biochem. Eng. J. 25 (2005) 125-140), and thus may not be applicable to more complex protein mixtures.

Also, while commercial programs of various quality and validity for simulation of separation processes exist, e.g. Aspentech in U.S. Pat. No. 5,666,297, all polypeptide and system specific parameters, such as the steric factor $\sigma$, the characteristic charge $v$, and the equilibrium constant $K$ in the e.g. the SMA isotherm description and mass transfer coefficients, basically must be determined separately for each component in the mixture. Determination of peptide specific parameters, however, usually requires pure gram-amounts of each component in the mixture. High through-put screening (HTS) techniques in ion-exchange batch adsorption mode have recently been applied in an effort to minimize consumption of pure protein for modelling (see, e.g., Rege et al., Sep. Sci Technol. 38 (2003) 1499-1517, for displacement chromatography predictions).

Accordingly, a need still exists for a simple and adequate method for simulation and modelling of chromatographic separation of polypeptide mixtures, especially where the target protein and one or more impurities are related.

SUMMARY OF THE INVENTION

The present invention relates in one aspect to a method for determination of polypeptide specific parameter(s) of a mixture comprising a target polypeptide and a related impurity or impurities to be used in a simulation model of chromatographic separation using mathematical model(s).

In a further aspect of the invention, a method of simulation using above determined parameters, is provided.

The invention also relates to a computer system and a computer program for performing above method(s).

DEFINITIONS

Figure 1:
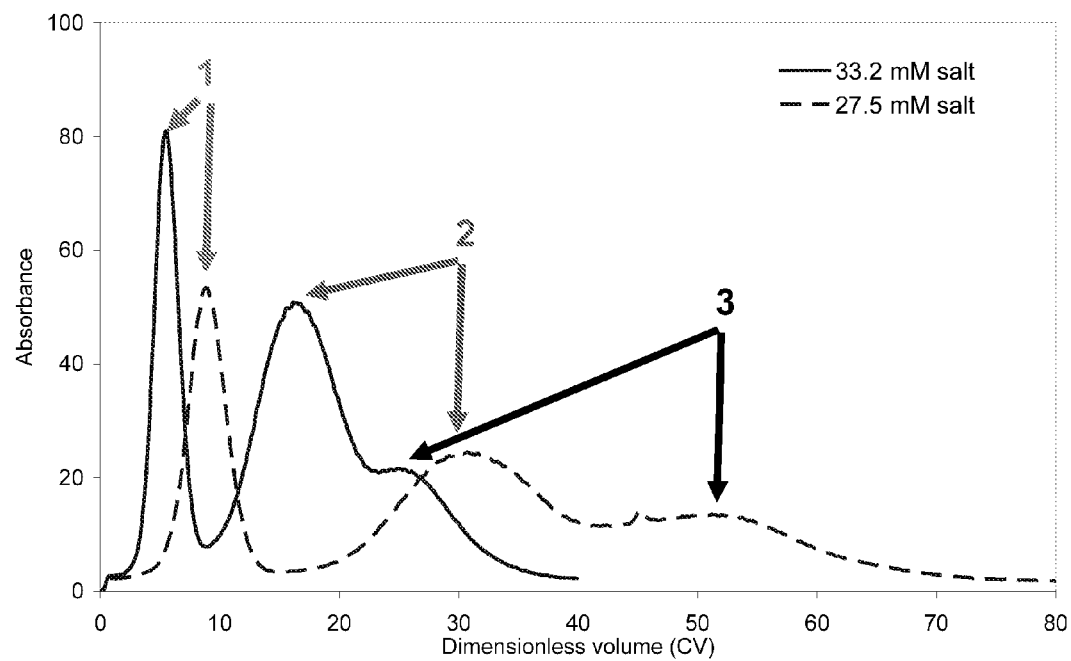
FIG. 1 shows the results of the pulse experiments as described in example 1.

The term "adsorption isotherm" as used herein means the relation between the quantity adsorbed in the solid phase (in/on the particle) and the composition in the liquid phase under equilibrium conditions at constant temperature. As examples the following may be mentioned: Langmuir type isotherm, a Bi-Langmuir type isotherm, Freundlich type isotherm, mass action type isotherm, steric mass action (SMA) isotherm, equation of state type isotherm, BET-type isotherm, Toth type isotherm, Radke-Praunitz type isotherm, Sips type isotherm, UNILAN type isotherm or other empirically or physical based adsorption isotherms (as described in Perry and Green, Perry's Chemical Engineers' Handbook, Chap. 16, $7^{th}$ Ed., McGraw-Hill, New York, 1997).

The term "chromatographic behavior" as used herein means the quantitative description of the chromatographic separation e.g. the elution order, retention, concentration of different components and elution profile also known as chromatogram.

The term "retention behavior" as used herein means e.g. the elution order and retention of different components.

The term "peptide specific parameter" describes parameters as used in mathematical models such as, e.g. the steric factor $\sigma$, the characteristic charge $v$, the equilibrium constant K in the SMA isotherm description and mass transfer coefficients.

The term "pulse experiment" is used herein to describe a method known to the skilled person within the field when a small amount of peptide or peptide mixture is applied onto a column followed by elution at different mobile phase compositions. In one aspect of the invention, the elution is a gradient elution. In another aspect of the invention, the elution is an isocratic elution.

The term "frontal analysis" (also called a breakthrough curve) is used herein to describe a method known to the skilled person within the field performed by continuously loading/supplying a feed to a column until the column is saturated with peptide and equilibrium conditions has occurred.

The term "mass balance" (also called a material balance) is used herein to describe an accounting of material entering and leaving a system. Fundamental to the balance is the conservation of mass principle, i.e. that matter can not disappear or be created.

The term "batch equilibrium experiment(s)" are used herein to describe the adsorption of a peptide or peptide mixture to a constant amount of resin (chromatographic particles) in a constant volume well-mixed batch system, e.g. HTS-system.

The term "fitting" is used herein to describe fitting of data (also called curve fitting) which is a procedure wherein parameters in an equation is matched to provide the best representation of experimental results/outcome/data. Data fitting can be performed using commercial available computer software e.g. TableCurve2D, SigmaPlot or MATLAB.

The term "mass transfer" also known as mass transport is used herein to describe mass transfer from the mobile to the stationary phase (Perry and Green, Perry's Chemical Engineers' Handbook, Chap. 16, 7th Ed., McGraw-Hill, New York, 1997) e.g. diffusion in and out of the particles. The term "impurity" as used herein means any product related impurity, host cell related impurity or process related impurity.

The term "host cell related impurity" as used herein means an impurity which is a peptide or a derivative of a peptide expressed by the cell cultivated to express the target peptide.

The term "process related impurity" as used herein means an impurity which is a component introduced in the manufacturing process of the target peptide e.g. leakage, cell culture media, additives such as e.g. detergents, salts, buffer components, enzymes, or modifiers. In one aspect of the invention, the process related impurity is a peptide.

The term "product related impurity" as used herein means an impurity which has structural resemblance to the target peptide. A related impurity has different chemical or physical structure than the target peptide, for instance a truncated form, an extended form (extra amino acids, various derivatives etc.), a deamidated form, an incorrectly folded form, a form with undesired glycosylation including sialylation, oxidated forms, forms resulting from racemization, forms lacking amino acids in the intra-peptide chain, forms having extra amino acids in the intra-peptide chain, forms wherein an acylation has taken place on another residue than desired, pegylated, acylated or glycosylated impurities, oxidated and deaminated forms, and many others.

The terms "polypeptide" and "peptide" and "protein" are used interchangeably herein and means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The following parameter abbreviations are used herein:
c: Mobile phase concentration [mol/L]
$c_S$: Salt concentration [mol/L]
$c_F$: Feed concentration
CV: Number of column volumes, dimensionless
i: Component index
TC: Target component
K: Equilibrium constant
Kd: Exclusion factor
v: Characteristic charge of the protein
Pe: Peclet number, dimensionless
q: Solid phase concentration [mol/L pore]
V: Dimensionless volume (CV)
$V_R$: Retention volume (CV)
$V_{mix}$: Mixer volume (CV)
x: Dimensionless length
ϵ: Porosity between particles
$\epsilon_p$: Porosity in particles
Λ: Capacity [mol/L pore]
σ: Steric factor
PDE: Partial Differential Equation
ODE: Ordinary Differential Equation

DESCRIPTION OF THE INVENTION

In order to perform simulation of chromatographic behaviour it is, for many of the current simulation models, necessary to determine one or more peptide-specific parameters such as e.g. the steric factor σ, the characteristic charge v, the equilibrium constant K, and mass transfer coefficients, for each peptide present in the mixture in pure form. These determinations are typically made using low column loads so that the isotherm can be assumed to be linear during the entire elution. While such determinations can be simple enough when each peptide in the mixture is a model protein commercially available in pure form, the situation is more complex for mixtures of closely related peptides or peptide analogs, such as, e.g., a reaction mixture containing a target peptide and one or more closely related impurities or by-products. Since many of the peptides are present only in small amounts, obtaining sufficient amounts of each peptide component in pure form can be time-consuming and, practically, close to impossible.

It has now been found that peptide-specific parameters for modelling purposes can be determined directly in the mixture of peptides, e.g., a target peptide and a related impurity or related impurities. Even though, at least in theory, the application of a peptide mixture could have increased the risk for non-linear conditions since a higher column loading may be necessary to detect each peptide component individually, actual comparisons of simulations based on parameters determined in peptide mixtures and experimental runs showed good agreement. For example, as shown in FIG. 1 (Example 1), pulse experiments were carried out on a mixture of a GLP-1 analog along with two diacylated variants and one triacetylated variant to determine characteristic charge and equilibrium constant, for use in simulation of ion-exchange chromatography. Subsequent comparison with an actual run revealed good agreement between the simulation and experimental results, thus verifying the adequacy of parameter estimation on peptide mixtures. This was also verified for impurity-containing peptide mixtures where the target peptide was MC-4, a human growth hormone variant, and an insulin analog.

Simultaneous determination of peptide-specific parameters can lead to a more straightforward application of modelling as a tool to simulate and model protein separation. True simulation and modelling of complicated chromatography systems have a variety of benefits, especially within the biopharmaceutical industry, and can be the technical solution to a number of problems such as, e.g.:

Optimization of existing processes according to Good Manufacturing Practice (GMP) processes—to save laboratory and full scale experiments and to obtain the best productivity and process economy including process integration.

Process control and process analytical tools (PAT) of new and existing GMP processes—for better understanding of the process, trouble-shooting, discovery of errors, handling of GMP deviations, to keep process in control according to new directions of regulatory authorities, to better control samples with varying composition, and to minimize subsequent experimentation and validation.

Process challenge, design of manufacturing facilities, and scale-up of new processes—to minimize laboratory and full scale experimentation and validation and to identify critical parameters, e.g. separation occurring during loading, design of mixer volumes etc.

Development of analytical chromatography methods and chromatographic purification including continuous processes—to obtain optimal purity of target protein or peptide and reduce lab and large scale experimentation to a minimum.

Problems caused by chemical or enzymatic reactions during purification e.g. degradation.

Thus, in one aspect, the invention relates to a method of determining peptide specific parameters to be used in a mathematical model for simulation of a chromatographic separation of a mixture comprising a target peptide and a related impurity or impurities, which method comprises the following steps:

(a) determining at least two peptide specific parameters by recording retention behaviour data of the target peptide and related impurity or impurities in said mixture and by fitting the obtained data to a mathematical model to calculate the peptide specific parameters, and, optionally (b) determining one or more peptide specific parameters by recording adsorption isotherm data of the target peptide optionally in a mixture with one or more of the related impurities and by fitting the obtained data to a mathematical model to calculate the peptide specific parameters, and, optionally (c) determining one or more peptide specific parameters by recording adsorption isotherm data of one or more of the related impurities and by fitting the obtained data to a mathematical model to calculate the peptide specific parameters, in which steps (a), (b) and (c) may be performed consecutively in any order or simultaneously.

In a further aspect, the method according to the invention comprises the following steps:
(a) determining at least two peptide specific parameters by recording retention behaviour data of the target peptide and related impurity or impurities in said mixture and by fitting the obtained data to a mathematical model to calculate said peptide specific parameters, and
(b) determining one or more peptide specific parameters by recording adsorption isotherm data of the target peptide and by fitting the obtained data to a mathematical model to calculate said peptide specific parameters, in which steps (a), and (b) may be performed consecutively in any order or simultaneously.

Figure 19:
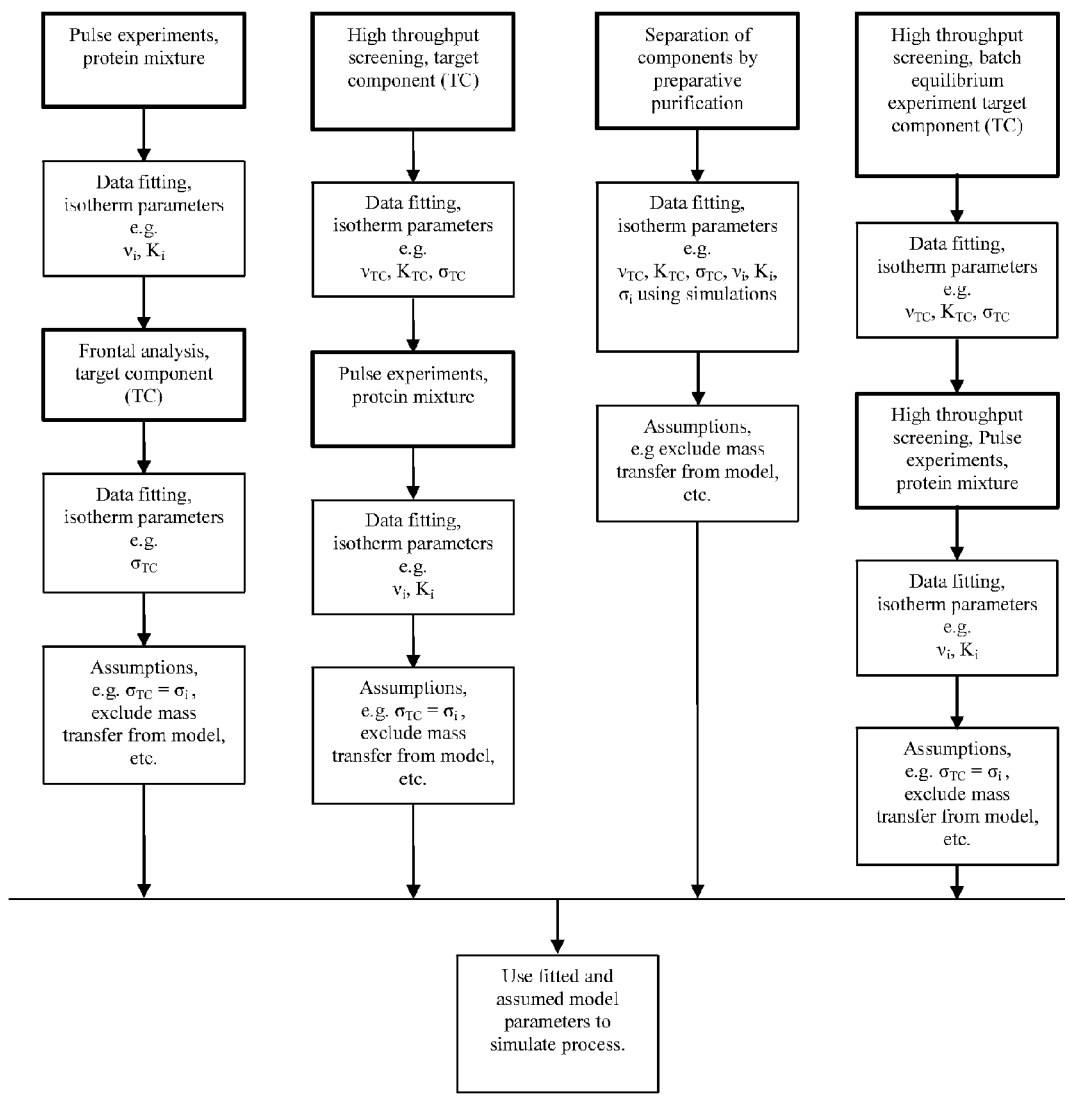
FIG. 19 illustrates several embodiments of the method according to the invention. The individual experiments described in the figure may be performed consecutively (in any order) or simultaneously.

FIG. 19 illustrates different embodiments according to the invention.

In a further aspect of the invention, the recording of the retention behaviour in step (a) is performed by a pulse experiment at different mobile phase compositions.

In yet a further aspect of the invention, the recording of the adsorption isotherm data is obtained by frontal analysis, or batch equilibrium experiment(s).

In yet a further aspect of the invention, the recording of the adsorption isotherm data is obtained by frontal analysis.

In yet a further aspect of the invention, the adsorption isotherm data is obtained by batch equilibrium experiment(s).

In yet a further aspect of the invention, the batch equilibrium experiment is performed by High Throughput Screening techniques, such as Robot technology.

In yet a further aspect of the invention, the recording of the retention behaviour is performed by High Throughput Screening techniques, such as Robot technology.

In yet a further aspect of the invention, the peptide specific parameter is determined by fitting the adsorption isotherm data to a Langmuir type isotherm, a Bi-Langmuir type isotherm, Freundlich type isotherm, mass action type isotherm, steric mass action (SMA) isotherm, equation of state type isotherm, BET-type isotherm, Toth type isotherm, Radke-Prausnitz type isotherm, Sips type isotherm, UNILAN type isotherm or other empirically or physical based adsorption isotherms.

In yet a further aspect of the invention, the isotherm is a steric mass action (SMA) isotherm.

In yet a further aspect of the invention, the recorded retention behaviour data is fitted to the following mathematical model represented by the equation:

$$V_{R,i} = V_{NR,i} + (1-\varepsilon)\varepsilon_p K_d K_i \left(\frac{\Lambda}{z_{salt} \cdot C_{salt}}\right)^{v_i} \quad (1)$$

wherein $Z_{salt}$ is the charge of the counter ion, $C_{salt}$ is the counter ion concentration, $\Lambda$ is the ionic capacity, $\varepsilon$ is the porosity between particles, $\varepsilon_p$ is porosity, $K_d$ is the exclusion factor, $V_{NR,i}$ is the retention volume for the peptides under non-retained conditions, $V_{R,i}$ is the retention volume, and i is the index for the peptide component, to determine the peptide specific parameters characteristic charge $v_i$ and the equilibrium constant $K_i$ for each component.

In yet a further aspect of the invention, the recorded adsorption isotherm data is fitted to the following mathematical model represented by the equation:

$$c_i = \frac{q_i}{K_i}\left[\frac{c_s}{\Lambda - \sum_i K_{d,i} \cdot q_i \cdot (v_i + \sigma_i)}\right]^{v_i} \quad (2)$$

wherein $\Lambda$ is the ionic capacity, $K_{d,i}$ is the exclusion factor, $\sigma_i$ is the steric factor, $v_i$ is the characteristic charge, $q_i$ is the solid phase concentration of peptide, $c_i$ is mobile phase concentration of peptide, $c_S$ is the counter ion concentration and $K_i$ is the equilibrium constant and i is the index for the peptide component, to calculate the peptide specific parameter the steric factor represented by $\sigma_i$.

In yet a further aspect of the invention, the adsorption isotherm data is recorded on the target peptide in pure form.

In yet a further aspect, the recorded adsorption isotherm data is fitted to the following mathematical model represented by the equation:

$$c_{TC} = \frac{q_{TC}}{K_{TC}}\left[\frac{c_s}{\Lambda - K_{d,TC} \cdot q_{TC} \cdot (v_{TC} + \sigma_{TC})}\right]^{v_{TC}} \quad (3)$$

wherein $\Lambda$ is the ionic capacity, $K_{d,TC}$ is the exclusion factor, $\sigma_{TC}$ is the steric factor, $v_{TC}$ is the characteristic charge, $q_{TC}$ is the solid phase concentration of peptide, $c_{TC}$ is mobile phase concentration of peptide, $c_S$ is the counter ion concentration and $K_{TC}$ is the equilibrium constant and TC is the index for the target peptide, to calculate one or more of the peptide specific parameters for the target peptide selected from the group consisting of the steric factor $\sigma_{TC}$, characteristic charge $v_{TC}$ and the equilibrium constant $K_{TC}$.

In yet a further aspect of the invention, the chromatographic separation method is selected from the group consisting of reverse phase high-performance liquid chromatography (RP-HPLC), reversed-phase liquid chromatography (RP-LC), straight phase chromatography, hydrophobic interaction chromatography (HIC), hydroxyapatite chromatography, ion exchange chromatography, affinity pseudo-affinity chromatography, metal chelate chromatography, precipitation, adsorption, gel filtration, size-exclusion chromatography (SEC) electrophoresis and the like, executed singly, sequentially or as mixed-modes.

In yet a further aspect of the invention, the chromatographic separation method is selected form the group consisting of ion exchange chromatography, RP-LC and HIC.

In yet a further aspect of the invention, the chromatographic separation method is ion exchange chromatography.

In yet a further aspect of the invention, said mixture comprises a target peptide and one related impurity.

In yet a further aspect of the invention, said mixture comprises a target peptide and at least two related impurities.

In yet a further aspect of the invention, said mixture comprises a target peptide and at least three related impurities.

In yet a further aspect of the invention, said mixture comprises a target peptide and at least four related impurities.

In yet a further aspect of the invention, said mixture comprises a target peptide and at least five related impurities.

In yet a further aspect of the invention, said mixture comprises a target peptide and at least six related impurities.

In yet a further aspect of the invention, said mixture comprises a target peptide and at least ten related impurities.

In yet a further aspect of the invention, the content of related impurity or impurities in said mixture is at least 1 ppm, at least 10 ppm, at least 100 ppm, at least 0.1%, at least 1%, at least 5%, at least 10%, at least 20%, at least 50%, at least 90%, at least 95%, or at least 99.9% measured based on the total weight of the target peptide and related impurity or impurities.

In yet a further aspect of the invention, the related impurity is a product related impurity, host cell related impurity and/or process related impurity.

In yet a further aspect of the invention, the related impurity is a product related impurity.

In yet a further aspect of the invention, the related impurity or impurities are identified by recording the retention behaviour and selected from the group consisting of the 1, 2, 3, 4, 5, 6, 7, 8, 9, and 10 or more impurities, or of the 5, 4, 3, 2 and 1 impurities, eluting closest to the target peptide.

In yet a further aspect of the invention, the related impurity or impurities are identified by recording the retention behaviour and selected from the group consisting of the 1, 2, 3, 4, 5, 6, 7, 8, 9, and 10 or more impurities, or of the 5, 4, 3, 2 and 1 impurities, eluting in the highest amounts compared to the target peptide.

In a further aspect of the invention, a method for simulation of chromatographic separation of a mixture comprising a target peptide and a related impurity or impurities using the peptide specific parameters as determined by the method according to the invention, is provided.

In yet a further aspect of the invention, the steric factor for the target peptide and/or the related impurity or impurities have an assumed value.

In yet a further aspect of the invention, the steric factor for the related impurity or impurities is assumed to be identical to that of the target peptide.

In yet a further aspect of the invention, the mathematical model used for simulation chromatographic separation is mass balance equation.

In yet a further aspect of the invention, the simulation is performed of a chromatographic separation of a mixture in industrial scale for optimization of an existing GMP process.

In yet a further aspect of the invention, the simulation is performed of a chromatographic separation of a mixture in industrial scale during scale-up of production.

In a further aspect of the invention, a computer system comprising a memory and a processor, the processor being programmed to carry out the method according to the invention, is provided.

In yet a further aspect of the invention, a computer program product comprising means for performing the method according to the invention, is provided.

Target Peptide

In an embodiment of the present invention the target peptide to be purified is selected from a polypeptide, an oligopeptide, a protein, an antibody, a receptor, a receptor ligand, a vira, as well as homologues, analogues and derivatives thereof. Preferred, though non-limiting examples, include glucagon, hGH, insulin, aprotinin, FactorVII, TPA, FactorVIIa, FFR-FactorVIIa, heparinase, ACTH, Heparin Binding Protein, corticotropin-releasing factor, angiotensin, calcitonin, insulin, glucagon-like peptide-1, glucagon-like peptide-2, insulin-like growth factor-1, insulin-like growth factor-2, fibroblast growth factors, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods, DPP IV, interleukins, immunoglobulins, complement inhibitors, serpin protease inhibitors, cytokines, cytokine receptors, PDGF, tumor necrosis factors, tumor necrosis factors receptors, growth factors and analogues as well as derivatives thereof. More preferred, though non-limiting, examples include glucagon, hGH, insulin, aprotinin, FactorVII, FactorVIIa, FFR-FactorVIIa, FVII variants having a modified Gla-domain, FVIII, FIX, FX, FXI, FXIII, MC4 peptides, heparinase, glucagon-like peptide-1, glucagon-like peptide-2 and analogues as well as derivatives thereof, such as Val$^8$GLP-1(7-37), Thr$^8$GLP-1(7-37), Met$^8$GLP-1(7-37), Gly$^8$GLP-1(7-37), Val$^8$GLP-1(7-36) amide, Thr$^8$GLP-1(7-36) amide, Met$^8$GLP-1(7-36) amide, Gly$^8$GLP-1(7-36) amide, Arg$^{34}$GLP-1$_{(7-37)}$, human insulin, and B28IsoAsp insulin. Each of these peptides constitutes an alternative embodiment of the present invention.

In one aspect of the invention, the target peptide is the main constituent of an intermediate process for production of an active pharmaceutical ingredient (API) or a final API.

Specific peptide examples of the above-mentioned method are separation of Arg$^{34}$GLP-1$_{(7-37)}$ and Arg$^{34}$GLP-1$_{(9-37)}$ by cation exchange chromatography, human insulin and B30 human insulin ethyl ester by anion exchange chromatography, B28IsoAsp insulin and DesB23-30 insulin by anion exchange chromatography, prothrombin and des-γ-carboxy-Glu prothrombin by anion exchange chromatography, Arg$^{34}$GLP-1$_{(7-37)}$ and Arg$^{34}$GLP-1$_{(10-37)}$ by anion exchange chromatography, Lys$^{B29}$-(N-ε(α-tetradecanoyl))-desB30 insulin and DesB30 insulin by cation exchange chromatography, Lys$^{B29}$-(N-ε(α-tetradecanoyl))-desB30 insulin and Lys$^{B29}$-(N-ε(α-tetradecanoyl))-A1-(N-ε(α-tetradecanoyl))-desB30 insulin by cation exchange chromatography, aprotinin and Des-Arg-Pro-aprotinin by cation exchange chromatography, and Glucagon$_{(1-29)}$ and Glucagon$_{(6-29)}$ by anion exchange chromatography.

Typically, the target peptide can be produced by standard recombinant techniques. The DNA sequence encoding the parent peptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, *Molecular Cloning: A Laboratory Manual*, Cold Spring Harbor Laboratory Press, New York, 1989). The DNA sequence encoding the peptide may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the peptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the peptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracycline chloramphenicol, neomycin, hygromycin or methotrexate.

To direct a peptide into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, vira, e.g. baculo virus, yeast, fungi, insect cells and higher eukaryotic cells. Examples of suitable host cells well known and used in the art are, without limitation, *E. coli, Saccharomyces cerevisiae*, or mammalian BHK or CHO cell lines.

Some of the peptides, in particular the oligopeptides, can be produced according to conventional organic peptide synthetic chemistry. The resulting synthetic mixture may then be chemically modified, e.g. by alkylation, acylation, ester formation or amide formation or the like, and purified, or purified as it is and then modified chemically as mentioned above.

The processes of the present invention can be particularly feasible for "industrial-scale" (or "large-scale") bulks of a target peptide. By the term "industrial-scale" is typically meant methods wherein the volume of the target peptide compositions is at least 100 L, such as at least 500 L, e.g. at least 1000 L, or at least 5000 L, or where the weight of the compositions is at least 100 kg, such as at least 500 kg, e.g. at least 1000 kg, or at least 5000 kg.

The peptides can be produced by a method which comprises culturing or fermenting a host cell containing a DNA sequence encoding the polypeptide and capable of expressing the polypeptide in a suitable nutrient medium under conditions permitting the expression of the peptide, after which the resulting peptide is recovered from the culture or fermentation broth. Hereinafter, culturing will be used to cover both culturing and fermenting and the like.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including, optionally lysis of cells, separating the host cells from the medium by centrifugation or filtration, precipitating the proteinaceous components of the supernatant or filtrate by means of a salt, e.g. ammonium sulphate, purification by conventional purification techniques, such as chromatographic techniques, if necessary, purification by ion exchange chromatography, and subsequently, subjecting to analytical tests, e.g. PAGE, IEF, if necessary, subjecting to further purification, if necessary, and isolation of the pure peptide.

During the recovery of the resulting peptide from the culture medium, but before purification by ion exchange chromatography, the mixture comprising the peptide and related impurities may optionally be chemically modified by conventional techniques, e.g. by alkylation, acylation, ester formation or amide formation or the like.

Parameter-Determination and Modelling

Any chromatographic separation or purification technique for peptides available to those skilled in the art may be modeled according to the invention. Examples of these techniques include, but are not limited to reverse phase high-performance liquid chromatography (RP-HPLC), reversed-phase liquid chromatography (RP-LC), straight phase chromatography, hydrophobic interaction chromatography (HIC), hydroxyapatite chromatography, ion exchange chromatography, affinity chromatography, metal chelate chromatography, precipitation, adsorption, gel filtration, size-exclusion chromatography (SEC) electrophoresis and the like, executed singly, sequentially or as mixed-modes. These chromatographic separation or purification methods are used extensively in production of peptides.

FIG. 19 outlines exemplary strategies to arrive at process simulation of a chosen chromatographic separation. Though a person of skill in the art can carry out and/or modify these strategies according to known methods in the art, some basic aspects are described in further detail below.

As described in FIG. 19, various strategies can be used to arrive at a simulated or modelled separation process with fitted or assumed model parameters. In one aspect, the invention provides for a method for simulation of chromatographic separation of a biopharmaceutical target protein or peptide from its related impurity or impurities using a mathematical model consisting of:

a) an adsorption isotherm describing solute (i.e., the peptide) equilibrium between the stationary and mobile phase, b) the overall mass balance of the chromatographic system, and optionally c) an expression describing mass transfer from the mobile to the stationary phase.

In one embodiment, process simulations can be based on any of the non-stationary 1D-models presented in Examples 1-3, with i components and salt, comprising a mass balance and an SMA isotherm as described, applied to ion exchange chromatography. The same principles can be applied to other chromatographic principles. The SMA isotherm is primarily developed for ion exchange chromatography, but may be used as an empirical model describing, e.g., reverse-phase chromatography, affinity chromatography, and hydrophobic interaction chromatography.

For simulation of chromatographic behaviour for one or more peptide it is, for many of the current simulation models, necessary to determine one or more peptide-specific parameters such as e.g. the steric factor $\sigma$, the characteristic charge $v$, the equilibrium constant K in the SMA isotherm description and mass transfer coefficients, for each peptide present in the mixture in pure form. As described herein, however, according to a preferred aspect of the invention, the above-described experiments to determine peptide-specific parameters can advantageously be performed on peptide mixtures, to simultaneously determine peptide-specific parameters (such as, e.g., isotherm parameters) for different peptide components. In one embodiment, the peptide mixture comprises a target peptide and at least one, at least two, at least three, at least four, at least five, at least six, or at least ten related impurities. In another embodiment, the content of related impurity or impurities in said mixture is at least 1 ppm, at least 10 ppm, at least 100 ppm, at least 0.1%, at least 1%, at least 5%, at least 10%, at least 20%, at least 50%, at least 90%, at least 95%, or at least 99.9% measured based on the total weight of the target peptide and related impurity or impurities. The peptide mixture may also comprise one or more impurities that are not related to the target peptide.

Retention behaviour related to peptide-specific parameters such as, e.g., the isotherm parameters characteristic charge (v) and equilibrium constant (K), is determined from retention volume ($V_R$) as a function of salt concentration ($c_s$ or $c_{salt}$) in, e.g., a pulse experiment. These experiment yield, e.g., the retention volume ($V_R$), determined from the centre of mass of the eluting peak by fitting the exponential modified Gauss (EMG) function to the response curve. In some cases the retention volumes are determined from the peak maxima. Such experiments can be carried out, e.g., by applying a small amount of sample onto the column, and chosen mobile phases used to elute the peptide or peptide mixture via either isocratic or gradient elution. The true retention volume of a solute equals the measured retention volume minus the dead volume. The dead volume from the injection valve to the detector can be determined by, e.g., injecting a small pulse of a suitable sample (e.g., NaNO3 solution) through an empty column with the distributers pressed together. The dead volume is then determined by fitting to the EMG-function to the eluting peak (see section about determination of the retention volume).

For example, to conduct a pulse-experiment on an ion-exchange column with isocratic elution, the column can be equilibrated, loaded with 100 µL of sample containing about 1 g protein/L of a peptide or peptide mixture solution, and the elution started. The salt (e.g., chloride) concentrations can be varied between different runs, where the lower concentration limit typically depends on the binding strength of the protein. The retention volume of the peptides is also determined at non-binding conditions, using, e.g., a high salt-concentration. For linear gradient elution, the gradient elution can be performed at different gradient volumes (e.g., in the range 20-60 CVs) using two buffer solutions at different salt (e.g., chloride) solutions. The column can be equilibrated and loaded with 100 µL of a sample containing about 1 g protein/L of a peptide or peptide mixture solution and the elution started.

Determination of steric factor ($\sigma$) can be made, e.g., by frontal analysis (i.e., breakthrough curve). For example, the column can be equilibrated with buffer and a suitable amount of sample solution, enough to ensure a plateau in the UV signal, is pumped through the system while bypassing the column. The UV detector can then be zeroed, and the sample solution passed through the column. The solution can be passed through the column well after the breakthrough until a close to constant signal is reached. The column can then be bypassed with a suitable amount of sample solution. The resulting experimental curve is a UV window which starts at zero, passes through a negative plateau and ends with the breakthrough followed by a near constant plateau and finally a step-up to zero from the second bypass. The procedure of bypassing has two purposes: it ensures a step injection originating close to the column and it provides a signal at the feed concentration to be compared with the plateau reached after the breakthrough and finally with the signal from the second bypass whereby one can estimate a possible shift in the detector response. The column is then regenerated and prepared for the next experimental salt concentration. It should be noted that, when determining the total amount of protein bound to the column, represented by the total area over the resulting curve, it should be corrected for void volume in the column (see FIG. 3).

One or more of the above experiments (e.g., pulse experiments, breakthrough curves) can also or alternatively be made in a high throughput screening mode. For example, protein solutions can be prepared with changing concentrations of salt and protein in a master plate by adding different volumes from a protein stock and buffer solutions. Samples from the master plate can be analyzed using, e.g., UV absorption to determine initial protein concentration. Particle plaques can be supplied in a working plate and protein solution then transferred from the master plate followed by mixing of the resin-liquid suspension until equilibrium between the solid and liquid phases is achieved. The equilibrium process can either be stopped by centrifugation or vacuum to remove the liquid phase. Samples of the supernatant can be analyzed using, e.g., UV absorption for determination of final protein concentration.

Data fitting can be made using, e.g., commercially available computer programs for, e.g., least-squares method, where you minimize the difference between experimental data and model (residual).

Certain assumptions facilitating the simulation can typically also be made. Some simple assumptions include:
(a) mass transfer coefficients such as the Stanton number (see, e.g., Moellerup and Hansen, supra) can typically be assumed identical for peptides of similar size or can be determined by, e.g., correlations (see, e.g., Rate-controlled Separations, Phillip C. Wankat, 1. edition, 1996, Mass transfer correlations, p. 376-383);
(b) the steric factor ($\sigma$) can be assumed to be identical for peptides of similar size;
(c) the exclusion factor ($K_d$) is equal to one for "small" peptides;
(d) mass transfer can be neglected;
(e) axial dispersion can be neglected;
(f) both mass transfer and axial dispersion can be lumped into the Pechlet number or Stanton number.
(g) peak broadening can be accounted for by adjusting the Pechlet number or Stanton number.
(h) different peptides can have different Pechlet numbers.

The model can be solved using a computer program such as, e.g., Comsol Multiphysics. The mathematical model can be solved using the General Form PDE (Comsol Multiphysics 3.2, September 2005, e.g. modeling guide, p. 241-243).

EXAMPLES

The following examples are illustrative only and are not intended to limit the scope of the invention in any way.

Example 1 Simulation of an Industrial Ion Exchange Step (Part 1): Determination of the Most Relevant Parameters Pulse experiments were carried out with a mixture containing liraglutide (Arg$^{34}$Lys$^{26}$(N$^\epsilon$-(γ-Glu-(N$^\alpha$-tetradecanoyl)))GLP-1(7-37)) (component 1 in FIG. 1), two diacylated variants (components 2 and 3 in FIG. 1), and one tri-acylated variant of GLP-1 on a 2.75 mL Source 30Q resin (GE Health Care), at pH 7.5, with a buffer system containing 10 mM Tris buffer, NaCl and 63% w/w ethanol. Pulse experiments were carried out by injecting a pulse of the mixture, followed by isocratic elution at different chloride concentrations which resulted in the recording of different retention volumes for the different proteins in the mixture (see FIG. 1).

Figure 2:
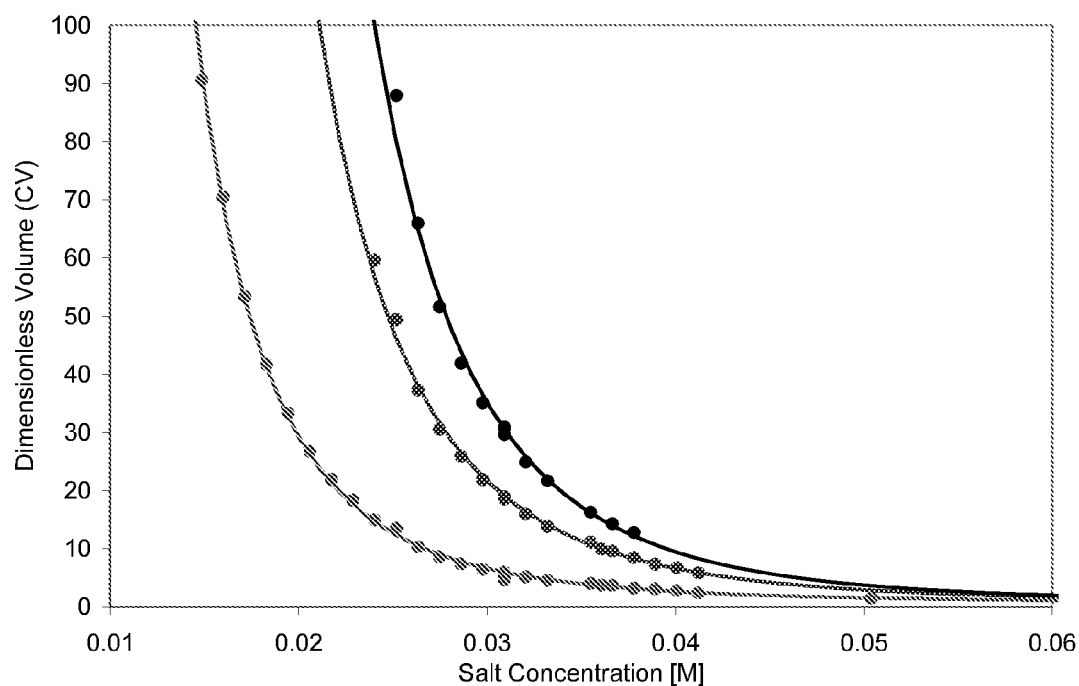
FIG. 2 shows the fit of characteristic charge and equilibrium constant as described in example 1. First curve from the left represents component 1, the second curve from the left represents component 2, and the third curve from the left represents component 3.

The retention volumes were fitted by conventional methods to the following expression:

$$V_{R,i} = V_{NR,i} + (1-\varepsilon)\varepsilon_p K_d K_i \left(\frac{\Lambda}{z_s \cdot c_s}\right)^{v_i} \quad (1)$$

where $Z_s$ is the charge of the counter ion (in this case chloride); $\Lambda$ is the ionic capacity (equivalents of ligands in the column per liter of pore-volume); $\varepsilon$ is the porosity between particles; and $\varepsilon_p$ is the porosity in particles (which, in this case, could be found in literature (Pedersen L., Ph.D. Thesis, Modeling Retention Volumes, Isotherms and Plate Heights for Whey Proteins in Anion Exchange Chromatography, IVC-SEP, DTU, 2003)). In this case, $\varepsilon$ was 0.45, $\varepsilon_p$ was 0.57 and $\Lambda$ was 0.30. $K_d$ is the exclusion factor which describes the percentage of the pores which the protein have access to, and $V_{NR}$ is the retention volume for protein under non-retained conditions (high salt concentration). In this example, $K_d$ was assumed to be 1 for all components, which means that the protein had access to all pores. This assumption meant that $V_{NR,I}$ was equal to the total porosity of the column ($\varepsilon_{total}=\varepsilon+(1-\varepsilon)\cdot\varepsilon_p=0.76$). Hereby $K_i$ (the equilibrium constant) and $v_i$ for each component could be determined from the fit of the equation to the data points (see FIG. 2, wherein the first curve from the left represents component 1, the second curve from the left represents component 2, and third curve from the left represents component 3).

The peptide specific parameters were found to be as described in Table 1.

TABLE 1

| Component | N | K |
|---|---|---|
| 1 | 3.66 | 0.00459 |
| 2 | 4.43 | 0.00251 |
| 3 | 4.78 | 0.00185 |
| 4 | 5.53 | 0.00120 |

Thus, the peptide specific parameters v and K for the different proteins were found from the pulse experiments.

Next, frontal analysis was carried out with pure liraglutide to determine the capacity of the resin at different loading concentrations of liraglutide.

Figure 3:
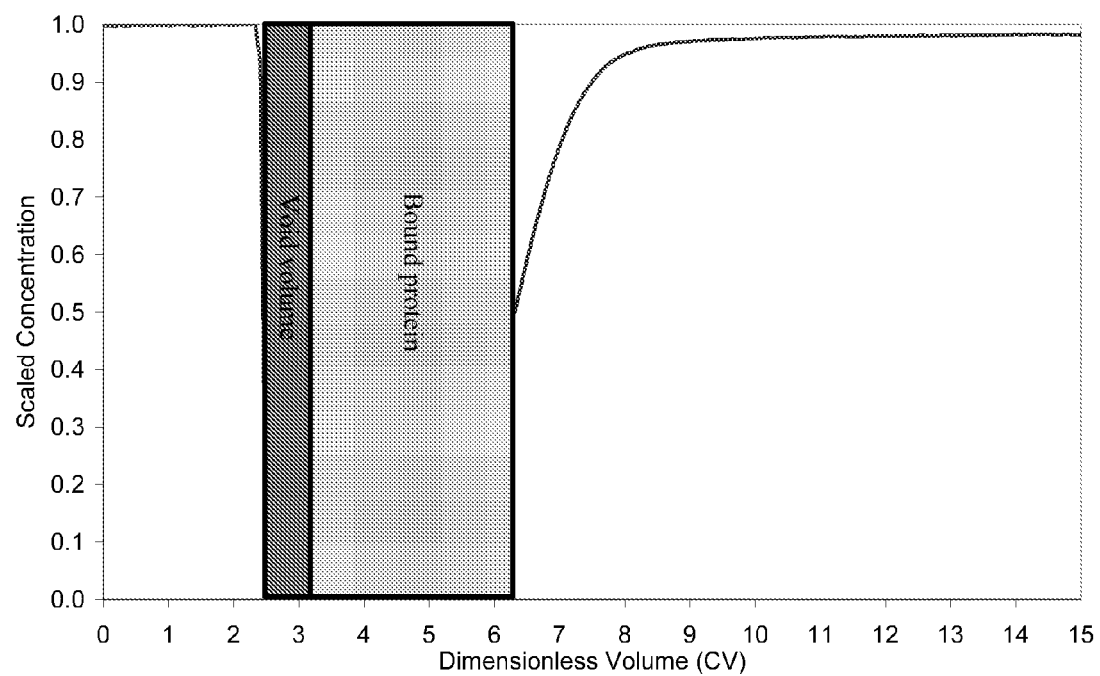
FIG. 3 shows the breakthrough curve of liraglutide as described in example 1.

FIG. 3 shows the breakthrough curve of liraglutide. Since the breakthrough curve was symmetric, the gray area represents bound peptide. Frontal analysis results obtained at different protein concentrations during loading were integrated to determine how much protein was bound on the column as described (Phillip C. Wankat, Rte-controlled separations, First edition 1990, 1194), and the steric factor was fitted for liraglutide to the equation below.

$$c_i = \frac{q_i}{K_i}\left[\frac{c_s}{\Lambda - \sum_i K_{d,i}\cdot q_i \cdot (v_i+\sigma_i)}\right]^{v_i}, \quad (2)$$

where q is the solid phase concentration of liraglutide, c is mobile phase concentration of liraglutide, $c_S$ is the chloride concentration from the frontal analysis experiments and σ is the steric factor which was fitted to be 4 for liraglutide. The index i is for each component.

Figure 4:
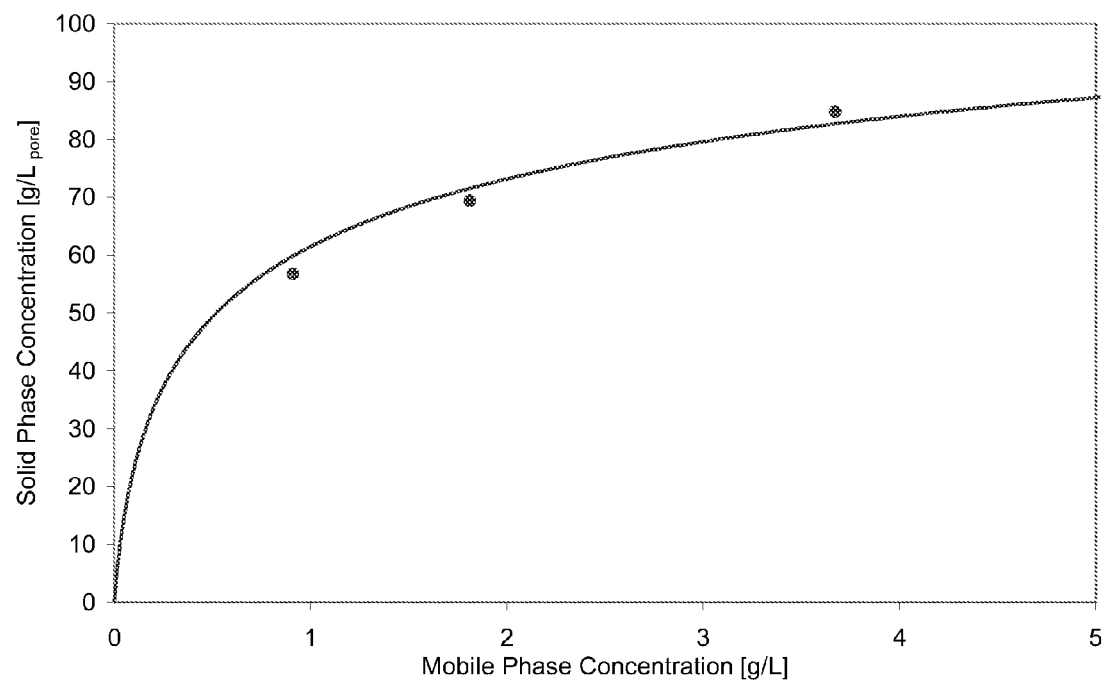
FIG. 4 shows the fit of the SMA isotherm to the experimental data as described in example 1.

FIG. 4. shows the fit of the SMA isotherm to the experimental data. The steric factor σ for the impurities was assumed to be equal to that of liraglutide.

The general form of the mass balance of the column is as described in Mollerup J., Hansen E., Kromatografisk teori, metoder og teknikker, 1$^{st}$ edition, DTU, Lyngby, Danmark, 2000.

$$\varepsilon\cdot v\frac{\partial c_i}{\partial z} + \varepsilon\frac{\partial c_i}{\partial t} + (1-\varepsilon)\frac{\partial s_i}{\partial t} - \varepsilon\cdot(D_f+D_a)\frac{\partial^2 c_i}{\partial z^2} = 0 \quad (4)$$

was rewritten to dimensionless form and to account for the following assumptions, (1) axial diffusion can be neglected (as e.g. described in Phillip C. Wankat, Rte-controlled separations, First edition 1990, 1194), (2) the mass transfer can be disregarded due to the fast diffusion in and out of the particles, and therefore the mobile phase concentration is assumed to be equal to the concentration in the pore i.e. $(1-\varepsilon)\cdot ds_i/dt=(1-\varepsilon)\cdot\varepsilon_p\cdot K_d\cdot d(c_i+q_i)/dt$, and (3) the collective contribution to the band broadening is described by axial dispersion which is expressed by the dimensionless Peclet number $$\frac{\partial c_i}{\partial x} + \varepsilon\frac{\partial c_i}{\partial V} + (1-\varepsilon)\varepsilon_p K_d\frac{\partial}{\partial V}(c_i+q_i) - \frac{1}{Pe_i}\frac{\partial^2 c_i}{\partial x^2} = 0 \quad (5)$$

x is the dimensionless length of the column and V is the dimensionless volume equal to the dimensionless time.

BC1: The boundary condition used for the mass balance in the inlet of the column is $c_i=c_{F,i}$ for all V and the boundary condition in the column outlet is (BC2)

$$\left.\frac{\partial c_i}{\partial x}\right|_{x=1} = 0 \text{ for all } V \quad (6)$$

Figure 8:
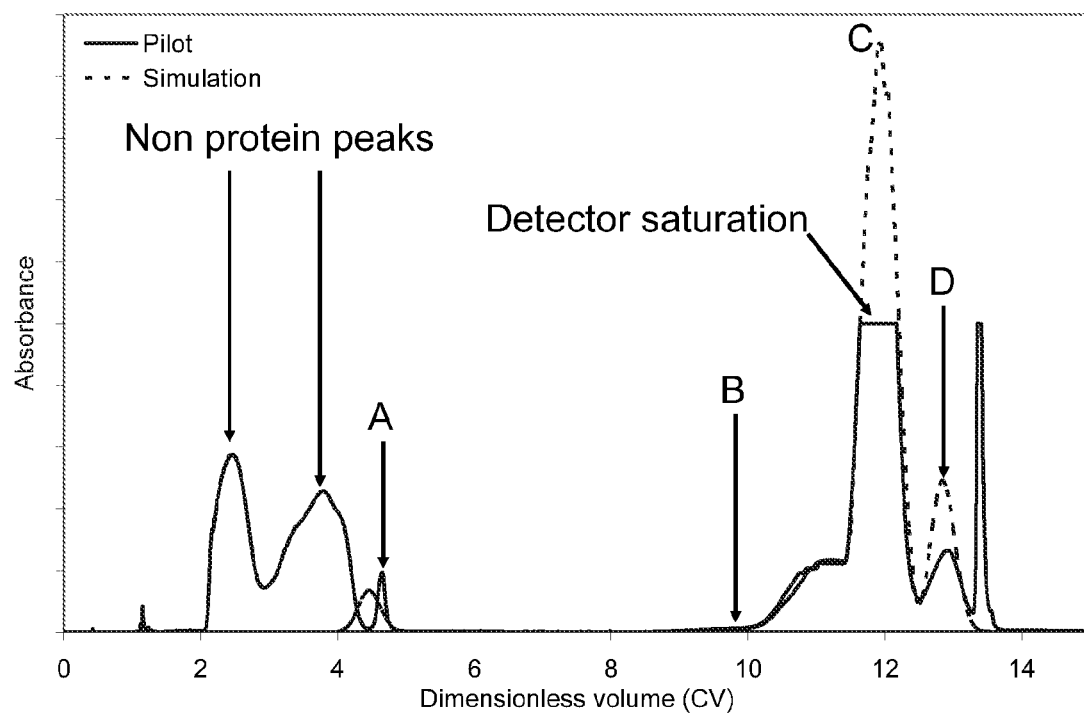
FIG. 8 shows the agreement between a simulation and an actual pilot scale run as described in example 2.

Based on the elution profile obtained in FIG. 8 the Peclet number is fitted such that the simulated peak width for each component matches the individual component peaks determined by the pulse experiment. In this experiment the Peclet number was determined by this method to be 75 for all components in the mixture in this experiment.

Hereby all protein specific parameters needed in the model have been determined or assumed as shown in Table 2 below.

TABLE 2

| Component | N | K | Σ | $K_d$ | Pe |
|---|---|---|---|---|---|
| 1 | 3.66 | 0.00459 | 4 | 1 | 75 |
| 2 | 4.43 | 0.00251 | 4 | 1 | 75 |
| 3 | 4.78 | 0.00185 | 4 | 1 | 75 |
| 4 | 5.53 | 0.00120 | 4 | 1 | 75 |

The model and the parameters were applied to COMSOL Multiphysics™ 3.2 in accordance with the User's Guide "Comsol multiphysics User's Guide", Version September 2005, Comsol 3.2 and the Modeling Guide "Comsol multiphysics Modeling Guide", Version September 2005, Comsol 3.2.

Figure 5:
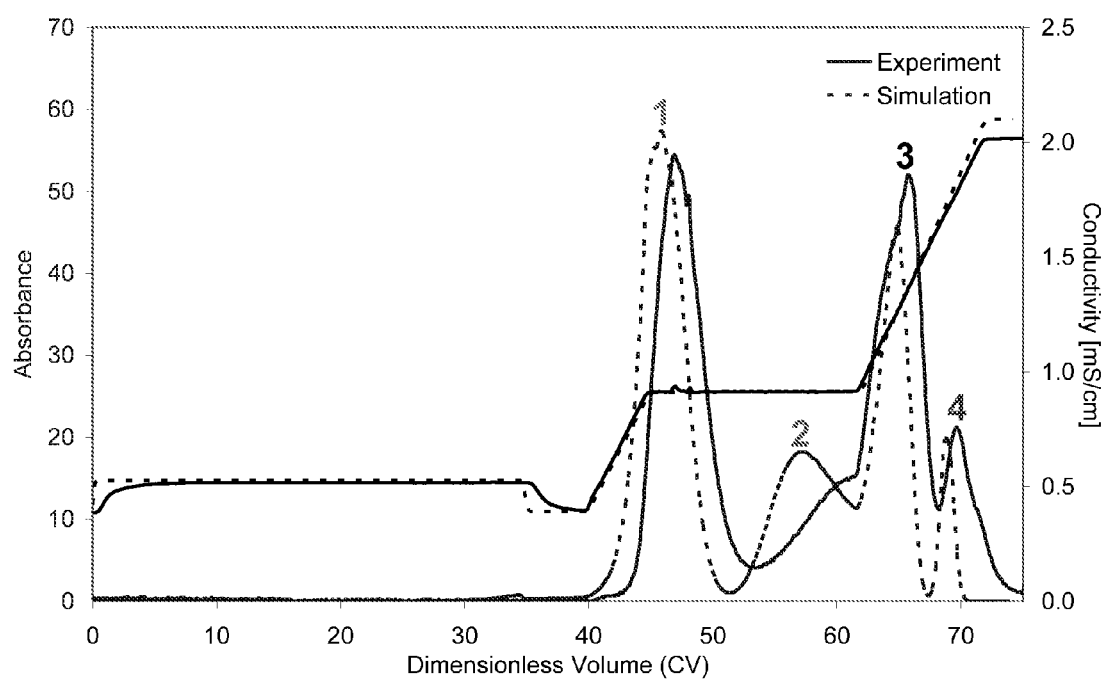
FIG. 5 shows a comparison of a simulated and an actual chromatogram as described in example 1.

Based on the above it was possible to simulate chromatographic runs. The solvents used were pH 7.5, 10 mM Tris buffer, NaCl and 63% w/w ethanol. The column used was a 2.75 mL Source 30Q. The sample for loading was 35 column volumes of a mixture containing 0.03 g protein per liter, split up into approximately 47% component 1, 24% component 2, 24% component 3, 5% component 4 and 18 mM of chloride. Elution was carried out by isocratic elution for 5 column volumes at 13.7 mM chloride followed by gradient elution from 13.7 mM chloride to 30.8 mM chloride over 5 column volumes followed by isocratic elution for 17 column volumes 30.8 mM chloride followed by gradient elution from of 30.8 mM chloride to 70.7 mM chloride over 10 column volumes. The mixer volume was set to 0.01 column volume in the simulation. FIG. 5 shows a comparison of a simulated and an actual chromatogram, showing good agreement.

Thus, in this Example we have determined the characteristic charge and equilibrium constant for four components and the steric factor for the target component. We have assumed identical steric factor and the exclusion factor for the other components. The Peclet number has been fitted to the actual chromatograms. The results show that by determining the most relevant parameters and making adequate assumptions it is possible to develop a method capable of separating four closely related proteins using computer simulations. This result was achieved with a number of simple experiments, computer simulations and just two test runs.

Example 2 Simulation of an Industrial Ion Exchange Step (Part 2): The Use of Simulation for Scale-Up and Trouble-Shooting Materials and Methods All chromatographic runs were performed in a pilot plant using Source 30Q resin and a NaCl/TRIS pH 7.5 buffer system.

All PDE's and ODE's were solved using Comsol Multiphysics™.

Theory

The simulations were based on the model presented in Example 1. A CSTR model was added to the column inlet to simulate a static mixer.

Introducing Boundary Conditions Used for the Mass Balance in Example 1:

CSTR:

$$(1) \quad \frac{\partial c_i}{\partial V} + \frac{c_i - c_{F,i}}{V_{mix}} = 0 \qquad (7)$$

Separating Variables:

$$(2) \quad \int_{c_{0,i}}^{c_i} \frac{1}{c_i - c_{F,i}} dc_i = \frac{1}{V_{mix}} \int_0^V dV \qquad (8)$$

BC1: Integrating Equation 2 Yields Boundary Condition at Column Inlet:

$$(3) \quad c_i = c_{F,i} + (c_{0,i} - c_{F,i})e^{\left(-\frac{V}{V_{mix}}\right)} \qquad (9)$$

BC2: A Neumann Boundary Condition is Used at Column Outlet:

$$(4) \quad \left.\frac{\partial c_i}{\partial x}\right|_{x=1} = 0 \text{ for all } V \qquad (6)$$

Figure 6:
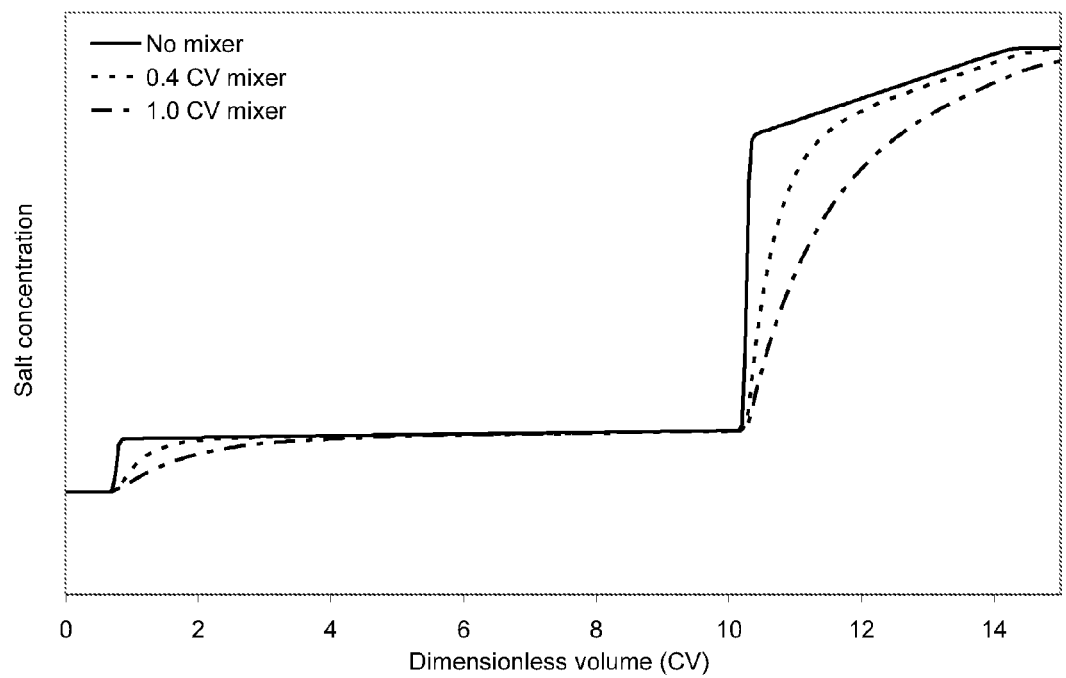
FIGS. 6 and 7 show the effect of a static mixer on the gradient response and elution profile (extra column effect) as described in example 2.
Figure 7:
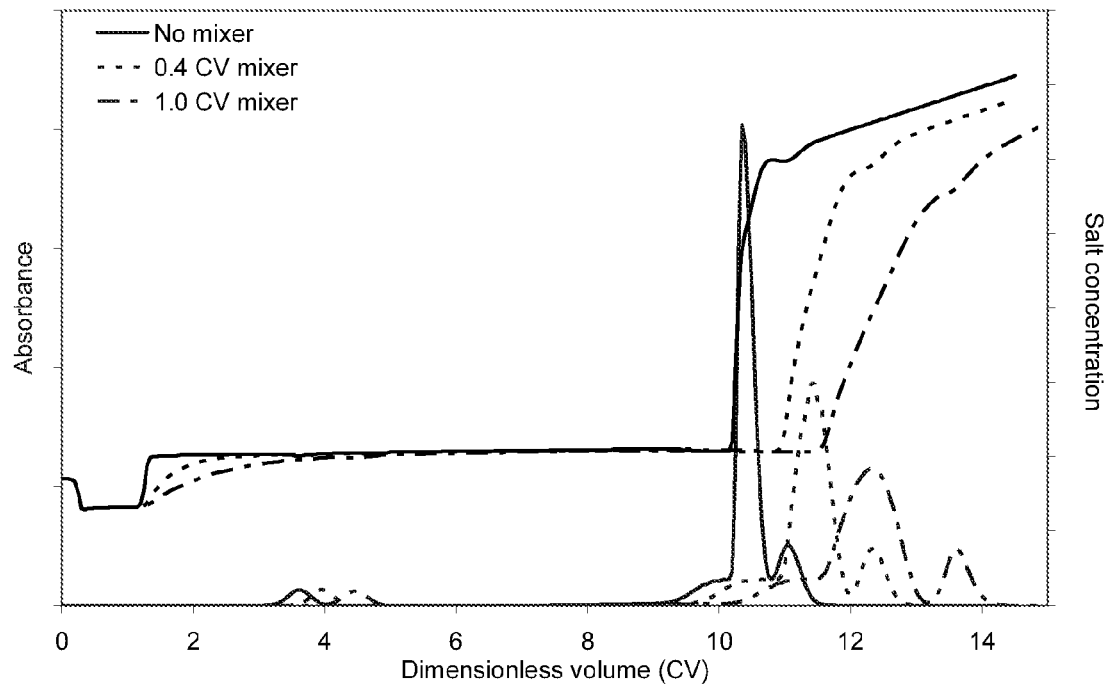

FIGS. 6 and 7 show the effect of a static mixer on the gradient response and elution profile (extra column effect).

As seen in FIG. 6, the programmed gradient becomes increasingly distorted as the mixer size increases.

FIG. 7 illustrates the significance of the effects of the extra column. As the mixer size increases from 0 to 1 CV, the elution profile changes and both retention and pool volume increases. If collection criteria by peak cutting is maintained, the yield will decrease as will the productivity.

Table 3 below shows the changes in retention volume, pool volume and yield caused by extra column effects.

TABLE 3

| Mixer size (CV) | 0 | 0.4 | 1.0 |
|---|---|---|---|
| $V_R$ (CV) | 10.3 | 11.5 | 12.4 |
| $V_{pool}$ (CV) | 0.95 | 1.1 | 1.5 |
| Yield [%] | 85 | 84 | 76 |
| Scaled productivity | 1.00 | 0.94 | 0.82 |

The process shown in FIG. 6 was successfully scaled 2000-fold (FIG. 8), keeping residence time constant (constant flow-rate in CV/h, Kidal and Elvang, BioPharm International, Mar. 1, 2006 (www.biopharminternational.com)) and using a mixer of 0.4 CV.

FIG. 8 shows the agreement between a simulation and an actual pilot scale run with a 0.4 CV static mixer.

A comparison of the impurity profile from RP-HPLC-analysis and simulation is presented in Table 4 below.

TABLE 4

Analytical results from pilot plant and simulated data.
Peaks from FIG. 8.

|  | A [%] | B [%] | D [%] | Yield | $V_{pool}$ (CV) |
|---|---|---|---|---|---|
| Starting material | 7.6 | 2.0 | 9.0 | NA | NA |
| Pilot plant | 0.0 | 0.1 | 1.0 | 84 | 1.1 |
| Simulation | 0.0 | 0.0 | 1.1 | 84 | 1.1 |

Trouble-Shooting in Pilot Plant.

Figure 9:
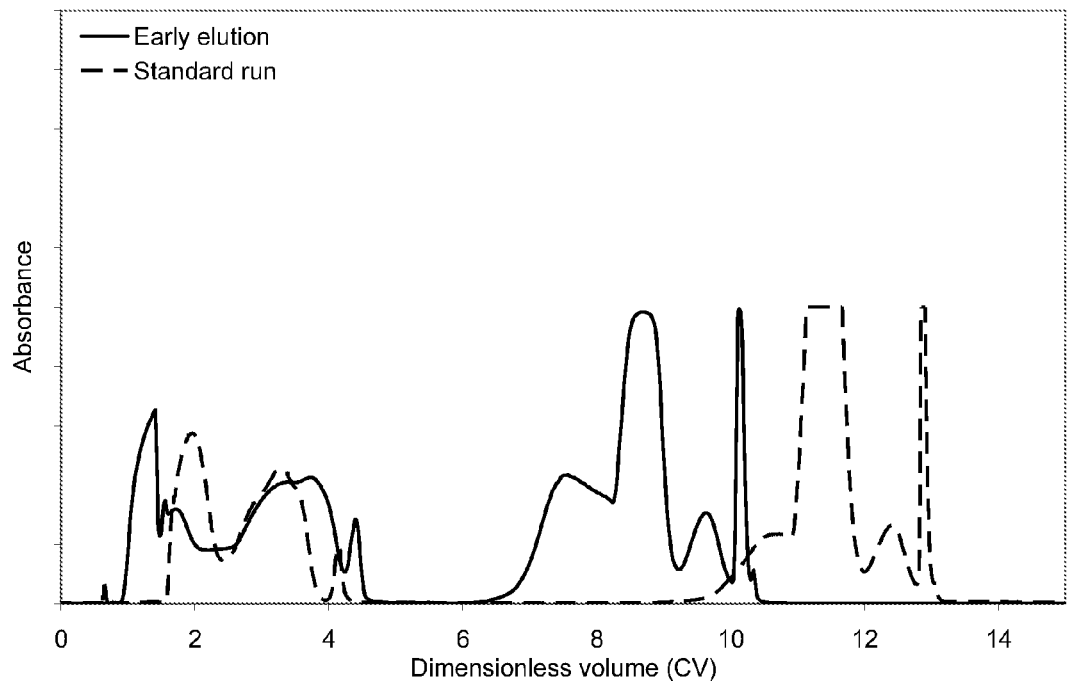
FIG. 9 shows a standard run and a run with early elution of target component in a pilot plant as described in example 2.

Early elution of target component was observed as seen in FIG. 9.

The following reasons for the early elution were suggested:

High salt in loading solution (observed)
High salt in buffer 1 (observed)
High salt in buffer 2 (checked and OK)
Wrong pH (checked and OK)

The different hypotheses were subsequently tested by simulation.

Figure 10:
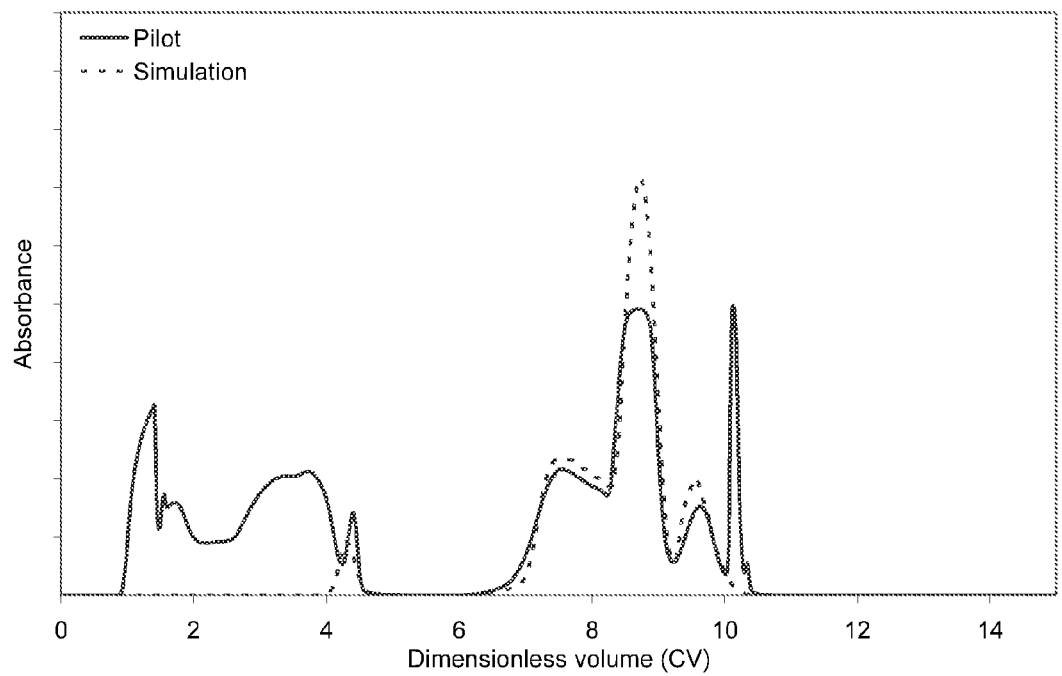
FIG. 10 shows a simulated chromatogram of high salt concentration in buffer 1 compared with an actual run as described in example 2.

Using a condition of high salt in buffer 1 demonstrated the observed effect shown in FIG. 10, which shows a simulated chromatogram of high salt concentration in buffer 1 as compared with an actual run.

As a consequence of the results obtained by simulation, buffer 1 was discarded. The subsequent run, performed with a different buffer, turned out as the standard run. Hereby, the problem was considered solved.

Conclusion

We have shown the advances of being able to simulate a chromatographic process and the impact of the static mixer on the chromatogram when a plant is designed or a process has been adapted to a given facility.

The simulated results show agreement with the actual chromatograms, impurity profiles, yields and pool volumes which indicates that the chosen model describes the actual process well.

It has been shown that computer simulations can be used to pinpoint the root cause of nonconformities and thus have an impact on process economics.

Example 3 Simulation of an Industrial Ion Exchange Step: The Use of Simulation for Optimization Materials and Methods All experiments were performed on an ÄKTA explorer 100 using Source 30Q resin and a NaCl/TRIS pH 7.5 (20° C.) buffer system with 63% w/w ethanol. A 2.75 mL (length 3.5 cm) column was used for parameter experiments.

All PDE's were solved using Comsol Multiphysics™.

Theory

Simulations were based on a non-stationary 1 D-model with i components and salt, comprising a mass balance with boundary conditions, and an SMA.

Mass balance [Mollerup J., Hansen E., *Kromatografisk teori, metoder og teknikker*, 1. edition, DTU, Lyngby, Denmark, 2000]

$$(1)\ \frac{\partial c_i}{\partial x} + \varepsilon \frac{\partial c_i}{\partial V} + (1-\varepsilon)\varepsilon_p K_d \frac{\partial}{\partial V}(c_i + q_i) - \frac{1}{Pe_i} \frac{\partial^2 c_i}{\partial x^2} = 0 \quad (5)$$

The integrated mass balance governs the distribution of salt and protein in both mobile and stationary phase throughout the column.

BC1: Boundary Condition at Column Inlet:

$$(2)\ c_i = c_{F,i} + (c_{0,i} - c_{F,i})e^{\left(-\frac{V}{V_{mix}}\right)} \quad (9)$$

BC2: A Neumann Boundary Condition is Used at Column Outlet:

$$(3)\ \left.\frac{\partial c_i}{\partial x}\right|_{x=1} = 0 \text{ for all } V \quad (6)$$

SMA isotherm [Brooks C. A., Cramer S. M., *Steric Mass-Action Ion Exchange: Displacement Profiles and Induced Salt Gradients*, AIChE Journal, Vol. 39, No. 12, 1992]:

$$(4)\ c_i = \frac{q_i}{K_i}\left[\frac{c_s}{\Lambda - \sum_i K_{d,i} \cdot q_i \cdot (v_i + \sigma_i)}\right]^{v_i} \quad (2)$$

The SMA isotherm describes the concentrations of protein in the mobile and stationary phase at equilibrium as a function of salt concentration.

Current Process

A purification step was developed and optimized by conventional methods i.e. trial and error optimization by laboratory experiments. The model presented in the theory section was applied to the process step and proved to be an important tool for troubleshooting [Hansen T B., Kidal S., *Simulation of an industrial ion exchange step (part 1): Determination of the most relevant parameters.* PREP 2006, poster] and [Kidal S., Hansen T B., *Simulation of an industrial ion exchange step (part 2): The use of simulation for scale-up and troubleshooting.* PREP 2006, poster] as shown above in Examples 1 and 2.

Figure 11:
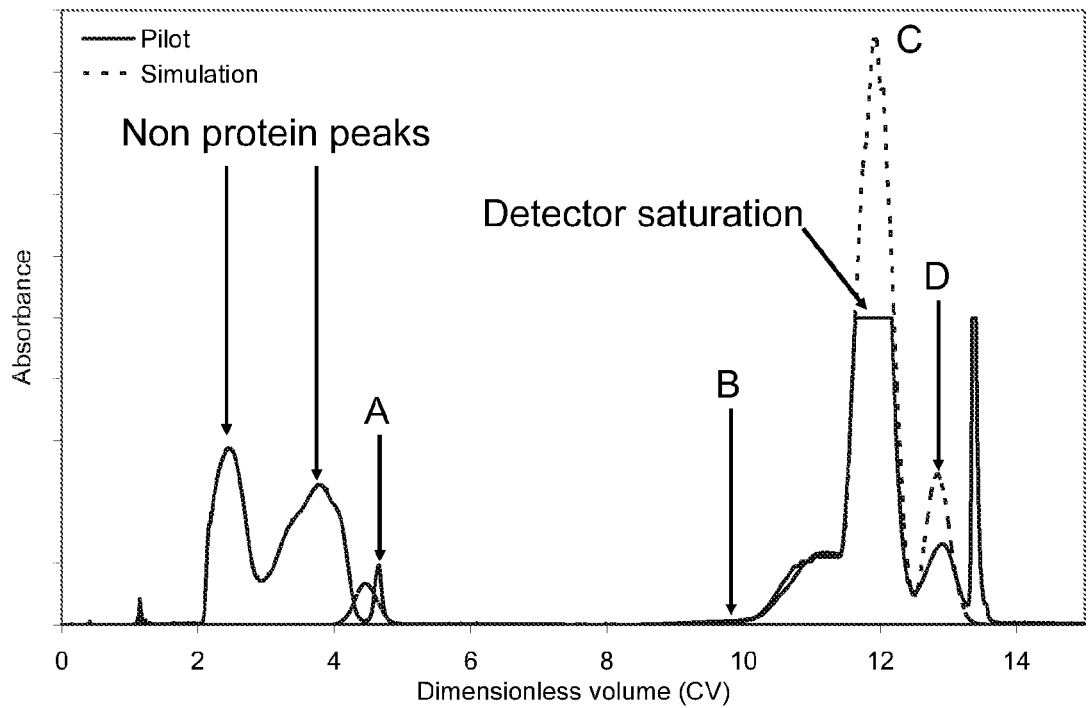
FIG. 11 shows a simulation and pilot run of a standard process. C is the target component as described in example 3.

FIG. 11 shows a simulation and pilot run of a standard process. C was the target component.

Figure 12:
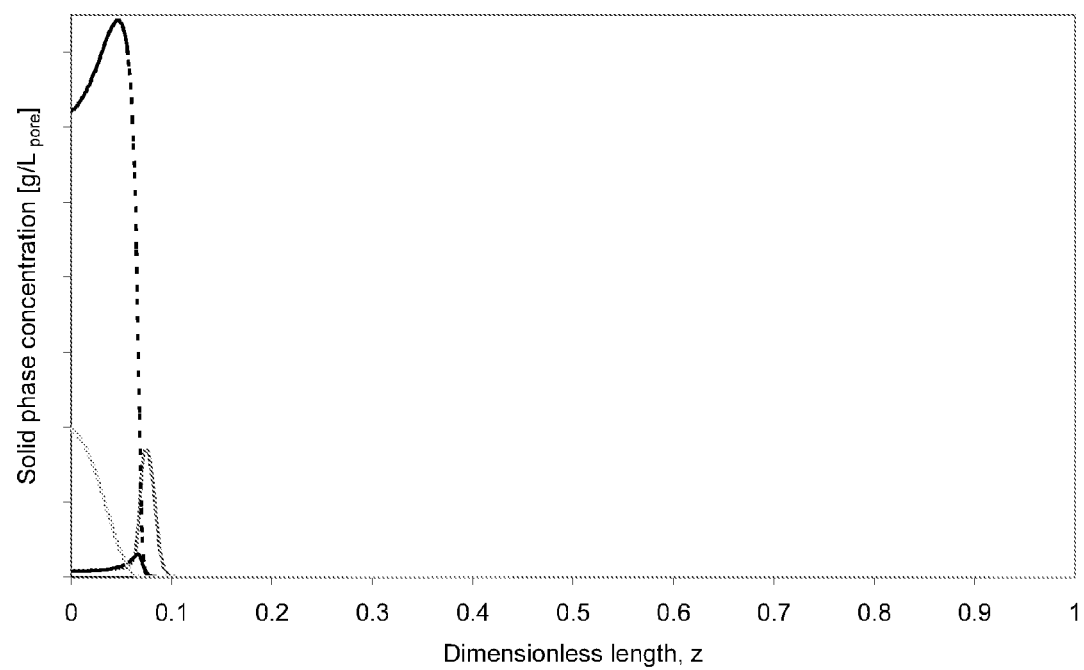
FIG. 12 shows a simulated concentration profile in solid phase in the column after loading as described in example 3.

FIG. 12 shows a simulated concentration profile in solid phase in the column after loading.

Optimization by Simulation

The next step was to optimize the productivity (g/h/Lresin) without compromising quality.

The following constraints during optimization were identified:

Loading solution (e.g., protein and/or salt concentration)
Scouting (i.e., testing different chromatographic conditions), such as loading (e.g., volume) and elution conditions (e.g., salt gradients and volume).

The process was optimized by trial and error, using approximately 40 computer simulations.

Figure 13:
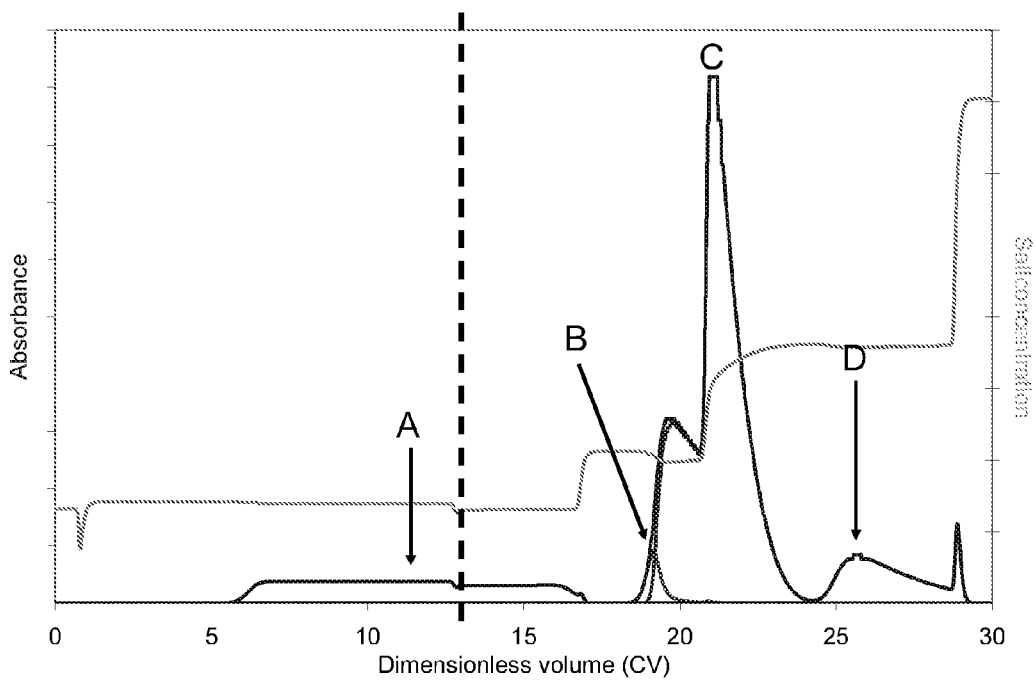
FIG. 13 shows a simulated chromatogram including both loading and elution for the optimized process as described in example 3. C is the target component.

FIG. 13 shows a simulated chromatogram including both loading and elution for the optimized process. C was the target component.

Figure 14:
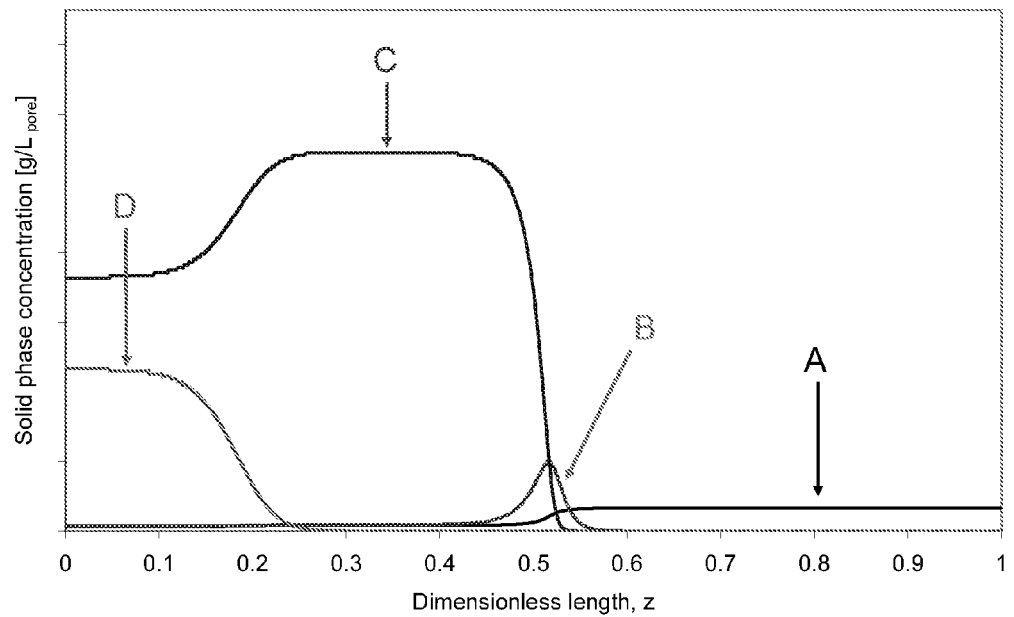
FIG. 14 shows a simulated concentration profile in solid phase in the column after loading for the optimized process as described in example 3. The profile shows intensive displacement of closely related impurities (A, B) by target component (C). Component D displaces component C.

FIG. 14 shows a simulated concentration profile in solid phase in the column after loading for the optimized process. The profile shows intensive displacement of closely related impurities (A, B) by target component (C). Component D displaces component C.

Figure 15:
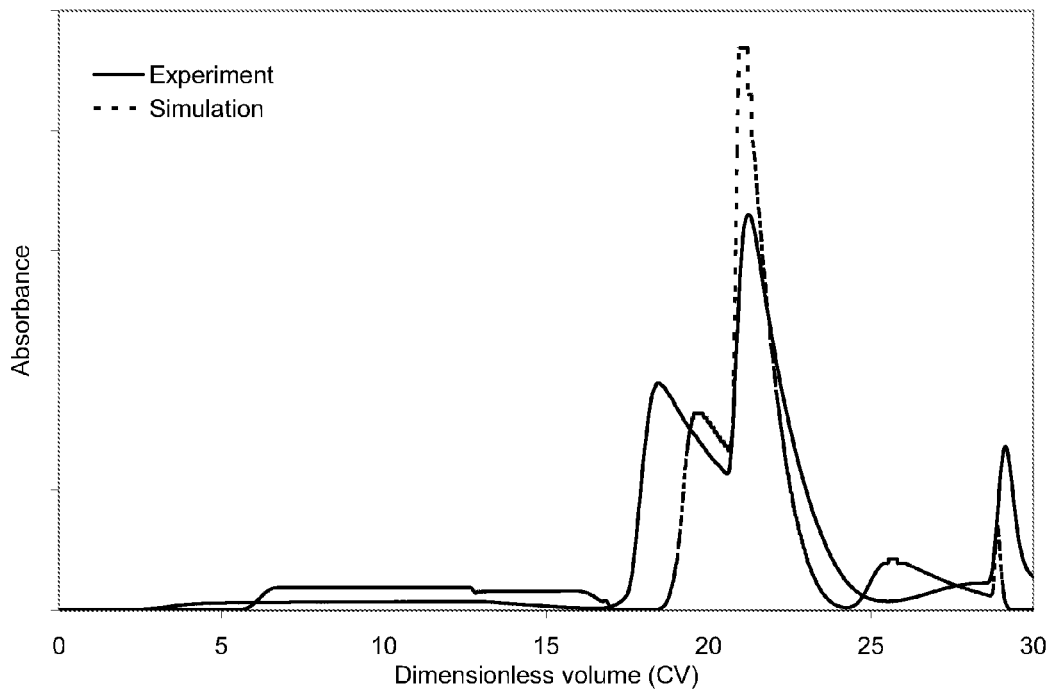
FIG. 15 shows an optimized process, with simulation compared to an actual laboratory run as described in example 3.

FIG. 15 shows the optimized process, comparing simulation to actual laboratory run.

Results

The chromatograms in FIG. 15 showed good agreement between simulation and experiment. A comparison of experimentally collected pools and simulations shown in Table 5 below further supports correlation.

TABLE 5

Comparison of simulated and experimental results.

|  | Starting material | Pool from simulation | Pool from experiment |
|---|---|---|---|
| A [%] | 15.0 | 0.0 | 0.0 |
| B [%] | 2.5 | 0.3 | 0.7 |
| D [%] | 12.5 | 0.0 | 0.0 |
| Pool volume (CV) | — | 5 | 6 |
| Yield [%] | — | 92 | 90 |
| Scaled productivity | — | 500% | 500% |

Conclusions

The results shown in FIG. 15 and Table 5 show that it is possible to use computer simulations to optimize an existing process and thereby improving the productivity—in this case five fold.

As a further step, an automated optimization routine using computer simulations can be implemented.

Example 4

Figure 16:
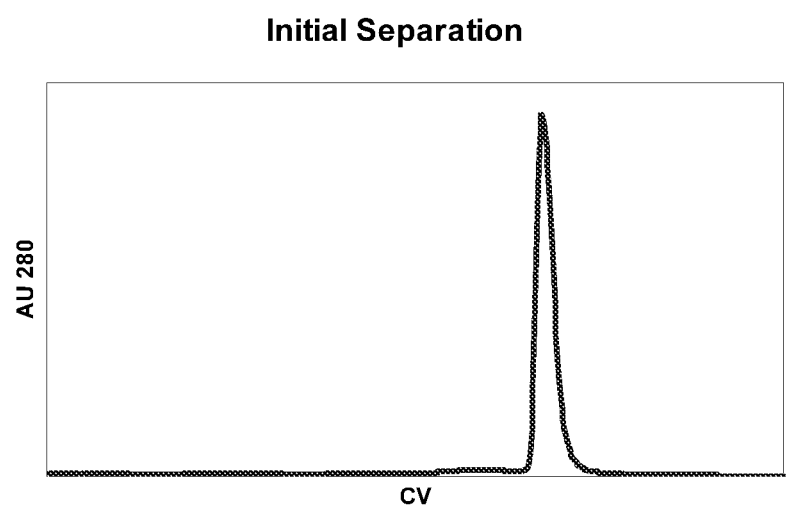
FIG. 16 shows an initial attempt to separate BSA and Lipolase as described in example 4.

Simulation and Optimisation of Purification Process for Separation of a Binary Protein Mixture of BSA and Lipolase A 1:1 sample of BSA and Lipolase based on weight was prepared by dissolving 0.5 g BSA and 0.5 g Lipolase in 1 liter of aqueous 50 mM Tris+50 mM Bis-Tris Propane, pH 8.0. In an initial separation experiment and attempt, 10.1 mL of the sample containing BSA and Lipolase was applied on a 5.03 mL DEAE Sepharose FF column (GE HealthCare, Uppsala, Sweden) at a constant flow rate of 50.5 mL/hour. The solvents used were A: 50 mM Tris+50 mM Bis-Tris Propane, pH 8.0 and B: 50 mM Tris+50 mM Bis-Tris Propane+1 M NaCl, pH 8.0. The column was equilibrated with solvent A and separation was carried out by gradient elution from 75 mM chloride to 1075 mM chloride over 10 column volumes. As shown in FIG. 16, no separation of the two components was obtained.

Figure 17:
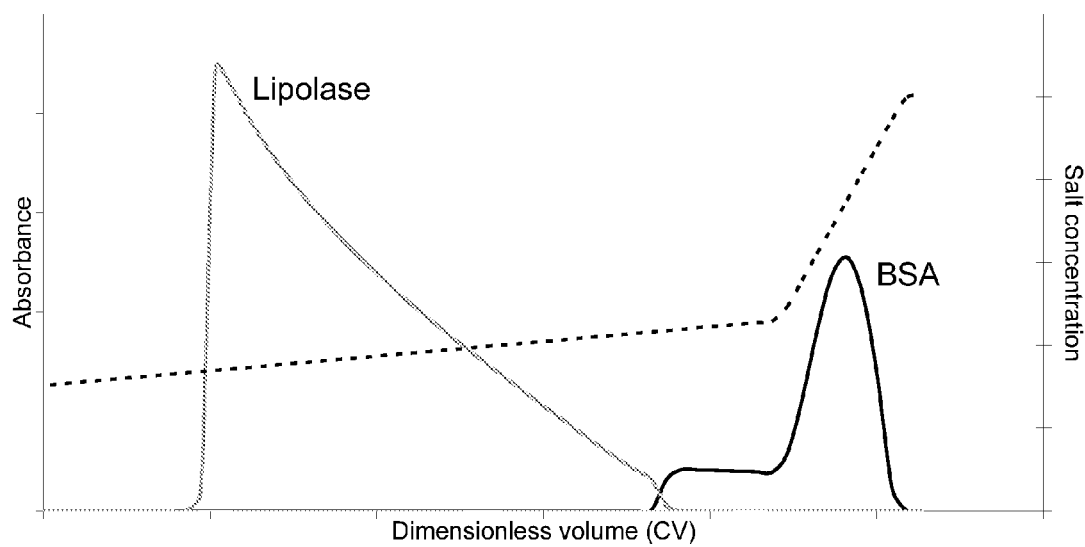
FIG. 17 shows a simulated separation of BSA and Lipolase as described in example 4.

Isotherm data derived from static capacity measurements were determined for BSA and Lipolase on a TECAN Freedom EVO robot system (TECAN, Männedorf, Switzerland) by methods in 96-well formats as described by Jack F. Kramarczyk (High-Throughput Screening of Chromatography Resins and Excipients for Optimizing Selectivity, Master of Science Thesis, Tufts University, August 2003). Pulse experiments for BSA and Lipolase were performed as described for GLP-1 components in Example 1. Characteristic parameters obtained for BSA and Lipolase by fitting and the model described in Example 1 were applied to the COMSOL Multiphysics™ 3.2 programme, and simulation resulted in the optimized separation depicted in FIG. 17.

Figure 18:
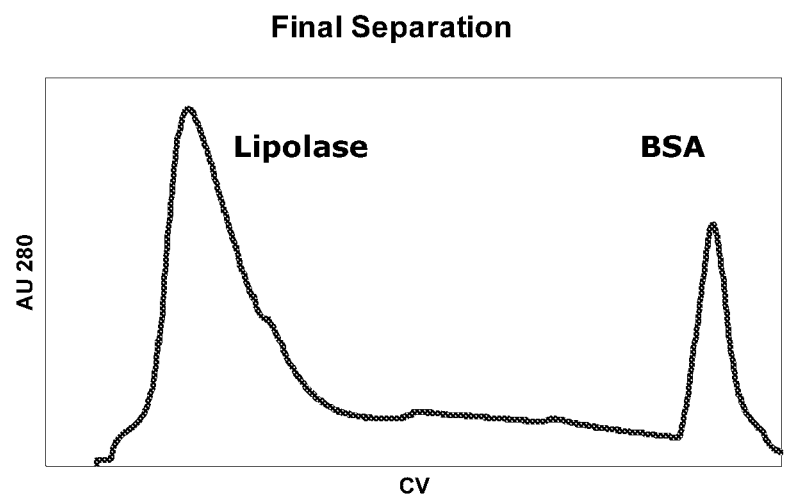
FIG. 18 shows an experimental verification of separation of BSA and Lipolase as described in example 4.

To verify the separation, the optimized experimental conditions with respect to both separation and load obtained from the simulation were applied to the separation system. Using the same basic solvents, the conditions of the final separation were:

The 5.03 mL DEAE Sepharose FF column was equilibrated with solvent A. The sample for loading was 20 column volumes of a mixture containing 1.0 g Lipolase and 1.0 g BSA in 1 liter of solvent A. Elution was carried out by gradient elution from 75 mM chloride to 115 mM chloride over 91 column volumes followed by gradient elution from 115 mM chloride to 250 mM chloride over 15 column volumes followed by isocratic elution for 5 column volumes at 250 mM chloride. The flow rate during loading and elution was 252.5 mL/hour. As shown in FIG. 18 an excellent separation of BSA and Lipolase was obtained at a higher loading, flow rate, and sample concentration compared to the initial experiment. Further, the separation profiles between the simulated and the experimental chromatogram (FIGS. 17 and 18) were very similar.

Example 5

Parameter Determination for Liraglutide and Related Impurities

This Example describes an exemplary procedure for determining v, σ, and K using pulse experiments with a mixture containing liraglutide ($Arg^{34}Lys^{26}(N^{\epsilon}-(\gamma-Glu-(N^{\alpha}-tetradecanoyl)))GLP-1(7-37)$), two diacylated variants, and one tri-acylated variant of GLP-1. See Example 1.

Materials and Methods

Chemicals.

Tris buffer (108382.1000) is from Merck (Darmstadt, Germany). NaCl (1.06404.1000) was from Merck (Darmstadt, Germany). 1 and 4 M HCl (1.00317.1000) were Merck (Darmstadt, Germany). 1 and 4 M NaOH (1.0698.1000) were from Merck (Darmstadt, Germany). Standard solutions for the pH meter calibration were from Radiometer (Copenhagen, Denmark). Ethanol was from Novo Nordisk (Denmark). Ion-free water (WFI) was used in all experiments.

Equipment.

The chromatography experiments were carried out on an Äkta explorer 100 system from GE Healthcare (Uppsala, Sweden). HP 8452A Diode Array spectrophotometer and WTW pH340 pH meter and buffer standard solutions were from Radiometer. The following column was used: Source 30Q (17-1275-01) from GE Healthcare (Uppsala, Sweden) packed in a HR 10/10 column from GE Healthcare (Uppsala, Sweden) packed at Novo Nordisk. The dimensions of the column were 1.0 cm in diameter and 3.5 cm in length which corresponded to a column volume of 2.75 mL. 150 mL Superloop was from GE Healthcare (Uppsala, Sweden).

Procedures.

Two buffer solutions were prepared by dissolving Tris and NaCl, in one of the two buffers, in WFI, then adding ethanol and titrating with HCl to pH 7.5 and finally adding WFI. The final concentration of tris was 20 mM and ethanol is 63% w/w in both buffers and 62.5 mM NaCl in one of them. The pH meter was calibrated with standard solutions at pH 7.000 and 10.012. The final concentrations of chloride in the two buffers were 13 mM to 70 mM.

The concentration in the feed solutions was determined on the HP 8452A spectrophotometer at 280 nm. The breakthrough curves were detected at 280 and 254 nm. The extinction coefficient was approx. 2.0 L/(g·cm).

Experimental Measurements

Pulse Experiments with Isocratic Elution:

The column was equilibrated with 10 CVs of buffer and the UV detector was zeroed. The column was loaded with 100 µL of a sample solution containing approx. 1 g protein/L and the elution was started. The chloride concentrations used varied from 13 mM to 70 mM. The lower limit depends on the binding strength of the protein. At the end of the elution the column was regenerated with 10 CVs of 1 M NaOH solution followed by 10 CVs 2 M NaCl pH 3.0 (CH3COOH) and finally 10 CVs buffer solution preparing the column to the next experimental salt concentration. The retention volume of the proteins was also determined using a 2 M NaCl buffer (nonbinding conditions). The flow-rates were 30, 60, 90 and 120 CV/h.

Pulse Experiments with Linear Gradient Elution:

The gradient elution was preformed at gradient volumes of 20, 30, 40, 50 and 60 CVs using two buffer solutions at 13 mM Cl— and 70 mM Cl—. The flow-rate was 60 CV/h. The column was equilibrated with 15 CVs of the starting buffer and the UV detector was zeroed. The column was loaded with 100 μL of a sample solution containing approx. 1 g protein/L and the elution started. At the end of the gradient the column was regenerated with 10 CVs of 1 M NaOH solution followed by 10 CVs 2 M NaCl pH 3.0 (CH3COOH) and finally 10 CVs buffer solution preparing the column to the next experimental salt concentration.

Estimation of the Dead Volumes:

The dead volume from the injection valve to the detector was determined by injecting a small pulse of NaNO3 solution through an empty column with the distributers pressed together. The dead volume was determined by fitting to the EMG-function to the eluting peak (see section about determination of the retention volume).

The dead volume including the mixer, through an empty column with the distributers pressed together and to the detector was determined by a shift from H2O (inlet A2) to 0.1 M NaNO3 (inlet B1). The dead volume can be determined from the resulting breakthrough curve by measuring the volume at 50% breakthrough.

Frontal Analysis:

The column was equilibrated with 20 CVs (column volumes) buffer and 40 mL of sample solution was pumped through the system while bypassing the column. The 40 mL was enough to ensure a plateau in the UV signal and the UV detector was zeroed. The sample solution was then passed through the column. The solution was passed through the column well after the breakthrough until a close to constant signal was reached. The column was then bypassed with 10 mL sample solution. The resulting experimental curve was a UV window which started at zero, passed through a negative plateau and ended with the breakthrough followed by a near constant plateau and finally a step-up to zero from the second bypass. The procedure of bypassing had two purposes: it ensured a step injection originating close to the column and it provided a signal at the feed concentration to be compared with the plateau reached after the breakthrough and finally with the signal from the second bypass whereby one can estimate a possible shift in the detector response. The column was regenerated with 10 CVs of 1 M NaOH solution followed by 10 CVs 2 M NaCl pH 3.0 (CH3COOH) and finally 10 CV buffer solution preparing the column to the next experimental salt concentration. All experiments were carried out at room temperature (20-25° C.)

Determination of the Retention Volume:

The retention volume was determined from the centre of mass of the eluting peak by fitting the exponential modified Gauss (EMG) function to the response curve. In some cases the retention volumes were determined from the peak maxima. The true retention volume of a solute equals the measured retention volume minus the dead volume.

High throughput screening could also be used in the above analysis. In such a setting, protein solutions are prepared with changing concentrations of salt and protein in a master plate by adding different volumes from a protein stock and buffer solutions. Samples from the master plate are analyzed using UV absorption to determine initial protein concentration. Particle plaques are supplied in a working plate and protein solution are transferred from the master plate followed by mixing of the resin-liquid suspension until equilibrium between the solid and liquid phases is achieved. The equilibrium process can either be stopped by centrifugation or vacuum to remove the liquid phase. Samples of the supernatant are analyzed using UV absorption for determination of final protein concentration.

Example 6—Separation of Components by Preparative Purification

Materials and Methods

The column (Source 30Q; 2.75 mL column) was equilibrated with 15 CVs of the starting buffer and the UV detector was zeroed. The column was loaded with 3 g/L resin of a sample solution containing approx. 3 g protein/L. The gradient elution was preformed at a gradient from 12% to 14% (high Cl— buffer) over 10 CVs then stepping to a new gradient from 80 to 100% (high Cl— buffer) over 4 CV using two buffer solutions at 13 mM Cl— and 70 mM Cl—. The flow-rate was 12 CV/h. At the end of the gradient the column was regenerated with 5 CVs of 1 M NaOH solution followed by 5 CVs 2 M NaCl pH 3.0 (CH3COOH) and finally 5 CVs buffer solution (low Cl— buffer).

Example 7—RPC Parameter Determination for Liraglutide and Related Impurities

This Example describes an exemplary procedure for determining v, σ, and K using the SMA isotherm on a reversed phase chromatography system. The parameters v and K were determined using data from pulse experiments with a mixture containing $Arg^{34}Lys^{26}$GLP-1(7-37), liraglutide ($Arg^{34}Lys^{26}(N^{\epsilon}$-(γ-Glu-($N^{\alpha}$-tetradecanoyl)))GLP-1 (7-37)) and a diacylated variant referred to as component 1, 2 and 3 respectively.

Materials and Methods

Chemicals.

Tris buffer (108382.1000) is from Merck (Darmstadt, Germany). NaCl (1.06404.1000) was from Merck (Darmstadt, Germany). 1 and 4 M HCl (1.00317.1000) were Merck (Darmstadt, Germany). 1 and 4 M NaOH (1.0698.1000) were from Merck (Darmstadt, Germany). Standard solutions for the pH meter calibration were from Radiometer (Copenhagen, Denmark). Ethanol was from Novo Nordisk (Denmark). Ion-free water (WFI) was used in all experiments.

Equipment.

The chromatography experiments were carried out on an Äkta explorer 100 system from GE Healthcare (Uppsala, Sweden). HP 8452A Diode Array spectrophotometer and WTW pH340 pH meter and buffer standard solutions were from Radiometer. The following column was used: ODDMS, Dohkai 120 Å, 15 μm, from FEF Chemicals (Køge, Denmark) packed in a Tricorn column from GE Healthcare (Uppsala, Sweden) packed at Novo Nordisk. The dimensions of the column were 1.0 cm in diameter and 2.5 cm in length which corresponded to a column volume of 1.96 mL. A-900 autosampler from GE Healthcare (Uppsala, Sweden) was connected to Äkta explorer 100.

Procedures.

Six buffer solutions were prepared by dissolving Tris and NaCl in WFI, then adding ethanol and titrating with HCl to pH 6.9 and finally adding WFI. The final concentrations were, 0.24% w/w Tris, 0.72% w/w NaCl and 0, 25, 31.5, 55, 70 and 80% w/w ethanol respectively corresponding to 0, 5.22, 6.50, 10.8, 13.2 and 14.7M. The pH meter was calibrated with standard solutions at pH 7.000 and 4.005. The concentration in the feed solutions was determined on the HP 8452A spectrophotometer at 280 nm. The breakthrough curves were detected at 280 and 254 nm. The extinction coefficient was approx. 2.0 L/(g·cm) at 280 nm.

Experimental Measurements

Pulse Experiments with Isocratic Elution:

The column was equilibrated with 5 CVs of buffer and the UV detector was zeroed. The column was loaded with 100 μL of a sample solution containing approx. 1 g protein/L and the elution was started. The ethanol concentrations used varied from 0 to 80% w/w. The lower limit depends on the binding strength of the protein. At the end of the elution the column was regenerated with 5 CVs of a solution containing 80% w/w ethanol, 0.24% w/w Tris and 0.72% w/w NaCl and finally 5 CVs buffer solution preparing the column to the next experimental ethanol concentration.

Estimation of the Dead Volumes:

See above

Determination of the Retention Volume:

The retention volume was determined from the centre of mass of the eluting peak by fitting the exponential modified Gauss (EMG) function to the response curve. In some cases the retention volumes were determined from the peak maxima. The true retention volume of a solute equals the measured retention volume minus the dead volume.

The retention volumes as a function of ethanol concentration for each component were fitted by conventional methods (see example 1) with the following assumed parameters: $\epsilon=0.45$, $\epsilon_p=0.57$, $\Lambda=1$, $K_d=1$, $Z_s=1$ and $V_{NR}=0.76$ (total porosity of the column). Table 6 shows the obtained model parameters.

TABLE 6

Obtained model parameters

| Component | N | K |
|---|---|---|
| 1 | 15.17 | 2.75E+13 |
| 2 | 13.91 | 4.26E+14 |
| 3 | 15.48 | 4.25E+17 |

High Loading Experiment

Finally, the steric factor ($\sigma$) was fitted by adjusting a simulated elution profile to an experimental elution profile under high loading conditions.

The solvents and column used are described above ("Procedures"). The sample for loading was 2.5 column volumes of a mixture containing 1 g protein per liter, split up into approximately 0.1% component 1, 99% component 2, 0.9% component 3 and 6.50M ethanol. Elution was carried out by isocratic elution for 0.5 column volumes at 5.22M of ethanol followed by gradient elution using a slope created from 8.34M ethanol to 8.62M ethanol over 24 column volumes, followed by gradient elution using a slope created from 8.62M ethanol to 9.62M ethanol over 2 column volumes as the target component (component 2) elutes. The mixer volume was set to 0.01 column volume in the simulation.

Results

Figure 20:
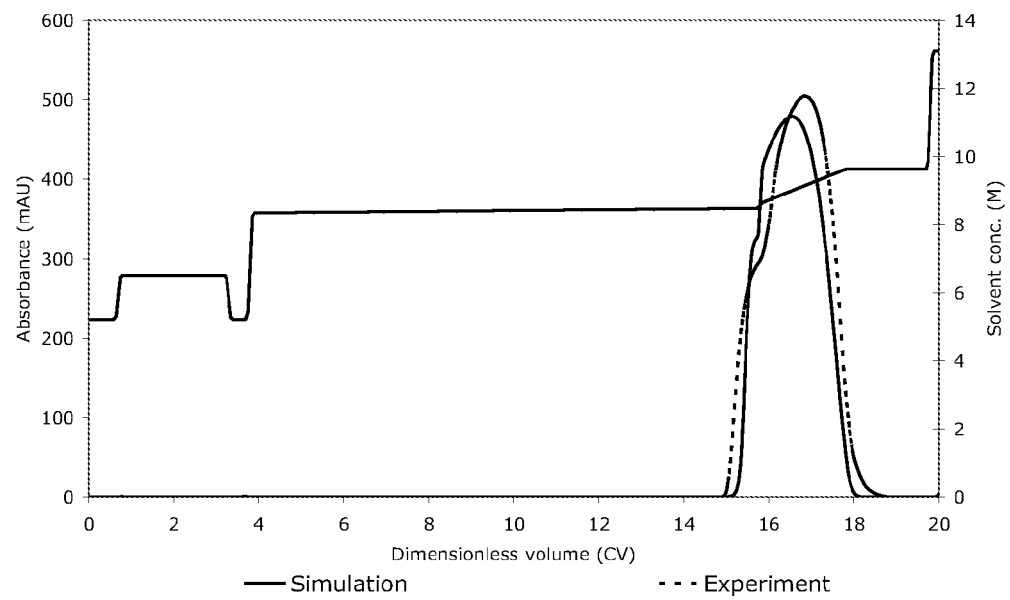
FIG. 20 shows a comparison of a simulated and an actual chromatogram of liraglutide and related impurities. Components 1 and 3 were not visible due to low concentration.

FIG. 20 shows a comparison of a simulated and an actual chromatogram, showing good agreement. The steric factor ($\sigma$) was set to −12.2 and was assumed identical for the two other components.

Exemplary Embodiments

The following paragraphs describe exemplary embodiments of the invention.

1. A method of determining peptide specific parameters to be used in a mathematical model for simulation of a chromatographic separation of a mixture comprising a target peptide and a related impurity or impurities, which method comprises the following steps:
   a) determining at least two peptide-specific parameters by recording retention behaviour data of the target peptide and related impurity or impurities in said mixture and by fitting the obtained data to a mathematical model to calculate the peptide-specific parameters, and optionally
   b) determining one or more peptide-specific parameters by recording adsorption isotherm data of the target peptide optionally in a mixture with one or more of the related impurities and by fitting the obtained data to a mathematical model to calculate the peptide-specific parameters, and optionally
   c) determining one or more peptide-specific parameters by recording adsorption isotherm data of one or more of the related impurities and by fitting the obtained data to a mathematical model to calculate the peptide-specific parameters,
   in which steps a), b) and c) may be performed consecutively in any order or simultaneously.

2. The method according to embodiment 1, comprising the following steps
   a) determining at least two peptide-specific parameters by recording retention behaviour data of the target peptide and related impurity or impurities in said mixture and by fitting the obtained data to a mathematical model to calculate said peptide-specific parameters, and
   b) determining one or more peptide-specific parameters by recording adsorption isotherm data of the target peptide and by fitting the obtained data to a mathematical model to calculate said peptide-specific parameters,
   in which steps a), and b) may be performed consecutively in any order or simultaneously.

3. The method according to any one of the embodiments 1-2, wherein the recording of the retention behaviour in step (a) is performed by a pulse experiment at different mobile phase compositions.

4. The method according to any one of the embodiments 1-3, wherein the recording of the adsorption isotherm data is obtained by frontal analysis, or batch equilibrium experiment(s).

5. The method according to any one of the embodiments 1-4, wherein the recording of the adsorption isotherm data is obtained by frontal analysis.

6. The method according to any one of the embodiments 1-5, wherein the adsorption isotherm data is obtained by batch equilibrium experiment(s).

7. The method according to any one of the embodiments 1-6, wherein the batch equilibrium experiment is performed by High Throughput Screening techniques, such as Robot technology.

8. The method according to any one of the embodiments 1-7, wherein the recording of the retention behaviour is performed by High Throughput Screening techniques, such as Robot technology.

9. The method according to any one of the embodiments 1-8, wherein the peptide specific parameter is determined by fitting the adsorption isotherm data to a Langmuir type isotherm, Bi-Langmuir type isotherm, Freundlich type isotherm, mass action type isotherm, steric mass action (SMA) isotherm, equation of state type isotherm, BET-type isotherm, Toth type isotherm, Radke-Praunitz type isotherm, Sips type isotherm, UNILAN type isotherm or other empirically or physical based adsorption isotherms.

10. The method according to any one of embodiments 1-9, wherein the isotherm is a steric mass action (SMA) isotherm.

11. The method according to any one of the embodiments 1-10, wherein the recorded retention behaviour data is fitted to the following mathematical model represented by the equation:

$$V_{R,i} = V_{NR,i} + (1-\varepsilon)\varepsilon_p K_d K_i \left(\frac{\Lambda}{z_{salt} \cdot c_{salt}}\right)^{v_i}$$

wherein $Z_{salt}$ is the charge of the counter ion, $C_{Salt}$ is the counter ion concentration, $\Lambda$ is the ionic capacity, $\epsilon$ is the porosity between particles, $\epsilon_p$ is porosity, $K_d$ is the exclusion factor, $V_{NR,i}$ is the retention volume for the peptides under non-retained conditions, $V_{R,i}$ is the retention volume, and i is the index for the peptide component, to determine the peptide specific parameters characteristic charge $V_i$ and the equilibrium constant $K_i$ for each component.

12. The method according to any one of the embodiments 1-11, wherein the recorded adsorption isotherm data is fitted to the following mathematical model represented by the equation:

$$c_i = \frac{q_i}{K_i}\left[\frac{c_s}{\Lambda - \sum_i K_{d,i} \cdot q_i \cdot (v_i + \sigma_i)}\right]^{v_i} \quad (2)$$

wherein $\Lambda$ is the ionic capacity, $K_{d,i}$ is the exclusion factor, $\sigma_i$ is the steric factor, $v_i$ is the characteristic charge, $q_i$ is the solid phase concentration of peptide, $c_i$ is mobile phase concentration of peptide, $c_S$ is the counter ion concentration and $K_i$ is the equilibrium constant and i is the index for the peptide component, to calculate the peptide-specific parameter the steric factor represented by $\sigma_i$.

13. The method according to any one of the embodiments 1-12, wherein the adsorption isotherm data is recorded on the target peptide in pure form.

14. The method according to embodiment 13, wherein the recorded adsorption isotherm data is fitted to the following mathematical model represented by the equation:

$$c_{TC} = \frac{q_{TC}}{K_{TC}}\left[\frac{c_s}{\Lambda - K_{d,TC} \cdot q_{TC} \cdot (V_{TC} + \sigma_{TC})}\right]^{v_{TC}} \quad (3)$$

wherein $\Lambda$ is the ionic capacity, $K_{d,TC}$ is the exclusion factor, $\sigma_{TC}$ is the steric factor, $v_{TC}$ is the characteristic charge, $q_{TC}$ is the solid phase concentration of peptide, $c_{TC}$ is mobile phase concentration of peptide, $c_S$ is the counter ion concentration and $K_{TC}$ is the equilibrium constant and TC is the index for the target peptide, to calculate one or more of the peptide specific parameters for the target peptide selected from the group consisting of the steric factor $\sigma_{TC}$, characteristic charge $v_{TC}$ and the equilibrium constant $K_{TC}$.

15. The method of any of embodiments 13-14, wherein at least one peptide-specific parameter for one or more related impurities is assumed identical or related to the corresponding peptide-specific parameter for the target peptide.

16. The method of embodiment 15, wherein at least one peptide-specific parameter selected from the group consisting of the steric factor $\sigma$, exclusion factor $K_d$ and Peclet number (Pe) of one or more related impurities is assumed identical to the corresponding peptide-specific parameter for the target peptide.

17. The method according to any one of the embodiments 1-16, wherein the chromatographic separation method is selected from the group consisting of reverse phase high-performance liquid chromatography (RP-HPLC), reversed-phase liquid chromatography (RP-LC), straight phase chromatography, hydrophobic interaction chromatography (HIC), hydroxyapatite chromatography, ion exchange chromatography, affinity pseudo-affinity chromatography, metal chelate chromatography, precipitation, adsorption, gel filtration, size-exclusion chromatography (SEC) electrophoresis and the like, executed singly, sequentially or as mixed-modes.

18. The method according to any one of the embodiments 1-17, wherein the chromatographic separation method is selected form the group consisting of ion exchange chromatography, RP-LC and HIC.

19. The method according to any one of the embodiments 1-18, wherein the chromatographic separation method is ion exchange chromatography.

20. The method according to any one of the embodiments 1-19, wherein said mixture comprises a target peptide and one related impurity.

21. The method according to embodiment 20, wherein said mixture comprises a target peptide and at least two related impurities.

22. The method according to embodiment 20, wherein said mixture comprises a target peptide and at least three related impurities.

23. The method according to embodiment 20, wherein said mixture comprises a target peptide and at least four related impurities.

24. The method according to embodiment 20, wherein said mixture comprises a target peptide and at least five related impurities.

25. The method according to embodiment 20, wherein said mixture comprises a target peptide and at least six related impurities.

26. The method according to embodiment 20, wherein said mixture comprises a target peptide and at least ten related impurities.

27. The method according to any one of the embodiments 1-26, wherein the content of related impurity or impurities in said mixture is at least 1 ppm, at least 10 ppm, at least 100 ppm, at least 0.1%, at least 1%, at least 5%, at least 10%, at least 20%, at least 50%, at least 90%, at least 95%, or at least 99.9% measured based on the total weight of the target peptide and related impurity or impurities.

28. The method according to any one of the embodiments 1-27, wherein the related impurity is a product related impurity, host cell related impurity and/or process related impurity.

29. The method according to embodiment 28, wherein the related impurity is a product related impurity.

30. The method according to any one of the embodiments 1-29, wherein the related impurity or impurities are identified by recording the retention behaviour and selected from the group consisting of the 1, 2, 3, 4, 5, 6, 7, 8, 9, and 10 or more impurities eluting closest to the target peptide.

31. The method according to any one of the embodiments 1-30, wherein the related impurity or impurities are identified by recording the retention behaviour and selected from the group consisting of the 1, 2, 3, 4, 5, 6, 7, 8, 9, and 10 or more impurities eluting in the highest amounts compared to the target peptide.

32. A method for simulation of chromatographic separation of a mixture comprising a target peptide and a related impurity or impurities using the peptide-specific parameters as determined by the method as defined in any one of the embodiments 1-31.

33. The method according to embodiment 32, wherein the steric factor for the target peptide and/or the related impurity or impurities have an assumed value.

34. The method according to embodiment 33, wherein the steric factor for the related impurity or impurities is assumed to be the same as that of the target peptide.

35. The method according to the embodiments 32-34, wherein the mathematical model used for simulation chromatographic separation is mass balance equation.

36. The method according to any one of the embodiments 32-35, wherein the simulation is performed of a mixture in industrial scale for optimization of an existing GMP process.

37. The method according to any one of the embodiments 32-35, wherein the simulation is performed of a mixture in industrial scale during scale-up of production.

38. A computer system comprising a memory and a processor, the processor being programmed to carry out the method of embodiments 32-37.

39. A computer program product comprising means for performing the method of any one of embodiments 32-37.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. A method of optimizing purification of a target peptide, comprising
    (i) determining peptide-specific parameters of the target peptide and at least one product related impurity by
        a) chromatographically separating a mixture comprising the target peptide and at least one product related impurity;
        b) recording retention behaviour data of the target peptide and at least one product related impurity;
        c) fitting the retention behaviour data to a mathematical model represented by equation (1) to calculate the peptide-specific parameters $v_i$ and $K_i$ for the target peptide and at least one product related impurity:

$$V_{R,i} = V_{NR,i} + (1-\varepsilon)\varepsilon_p K_d K_i \left(\frac{\Lambda}{z_{salt} \cdot c_{salt}}\right)^{v_i}, \quad (1)$$

wherein $Z_{salt}$ is the charge of the counter ion, $C_{salt}$ is the counter ion concentration, $\Lambda$ is the ionic capacity, $\epsilon$ is the porosity between particles, $\epsilon_p$ is porosity, $K_d$ is the exclusion factor, $V_{NR,i}$ is the retention volume under non-retained conditions, $V_{R,i}$ is the retention volume, i is the index for the target peptide or at least one product related impurity, $v_i$ is the characteristic charge, and $K_i$ is the equilibrium constant;
        d) recording adsorption isotherm data of the target peptide from the mixture or in a sample without the least one product related impurity; and
        e) fitting the adsorption isotherm data to a mathematical model represented by equation (2) to calculate the peptide-specific parameter $\sigma_i$ for the target peptide:

$$c_i = \frac{q_i}{K_i}\left[\frac{c_s}{\Lambda - \sum_i K_{d,i} \cdot q_i \cdot (v_i + \sigma_i)}\right]^{v_i} \quad (2)$$

wherein $\Lambda$ is the ionic capacity, $K_{d,i}$ is the exclusion factor, $\sigma_i$ is the steric factor, $v_i$ is the characteristic charge, $q_i$ is the solid phase concentration of peptide, $c_i$ is mobile phase concentration of peptide, $c_S$ is the counter ion concentration and $K_i$ is the equilibrium constant, and i is the index for the target peptide;

wherein the steric factor of the at least one product related impurity is assumed to be identical to the steric factor $\sigma_i$ for the target peptide; and (ii) simulating a chromatography using the calculated peptide-specific parameters $v_i$, $K_i$, and $\sigma_i$ to obtain optimized chromatography settings selected from the group consisting of loading solution and elution conditions for optimizing purification of the target peptide in a mixture with the at least one product related impurity;

(iii) applying the obtained optimized chromatography settings to chromatographic separation of the target peptide from the at least one product-related impurity and wherein the optimized chromatography settings improve productivity over chromatography that is not optimized.

2. The method according to claim 1, wherein the recording retention behaviour is performed by a pulse experiment at different mobile phase concentrations.

3. The method according to claim 1, wherein the recording retention behaviour is performed by a high throughput screening technique.

4. The method according to claim 1, wherein the recording adsorption isotherm data is performed by frontal analysis or a batch equilibrium experiment.

5. The method according to claim 4, wherein the recording adsorption isotherm data is performed by frontal analysis.

6. The method according to claim 4, wherein the recording adsorption isotherm data is performed by a batch equilibrium experiment.

7. The method according to claim 1, wherein the target peptide is selected from the group consisting of glucagon, hGH, insulin, glucagon-like peptide-1, FactorVII, FactorVIIa, FVIII, FIX, FXIII, and analogues or derivatives thereof.

8. The method according to claim 1, wherein the method is performed on an industrial-scale bulk of a target peptide.

9. The method according to claim 8, wherein the industrial-scale bulk is from at least 500 L to at least 5000 L.

* * * * *

UNITED STATES PATENT AND TRADEMARK OFFICE
CERTIFICATE OF CORRECTION

PATENT NO.       : 9,766,217 B2
APPLICATION NO.  : 12/440242
DATED            : September 19, 2017
INVENTOR(S)      : Kidal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1054 days.

Signed and Sealed this
Twenty-fifth Day of September, 2018

Andrei Iancu
*Director of the United States Patent and Trademark Office*